United States Patent
Piketty

(10) Patent No.: US 11,236,157 B2
(45) Date of Patent: Feb. 1, 2022

(54) TREATMENT OF SKIN LESIONS AND PRURITUS IN PRURIGO NODULARIS PATIENTS

(71) Applicants: GALDERMA HOLDING SA, La Tour-de-Peilz (CH); Chugai Seiyaku Kabushiki Kaisha, Tokyo (JP)

(72) Inventor: Christophe Piketty, Montargis (FR)

(73) Assignee: Galderma Holding SA, La Tour-de-Peilz (CH)

( * ) Notice: Subject to any disclaimer, the term of this patent is extended or adjusted under 35 U.S.C. 154(b) by 62 days.

(21) Appl. No.: 16/773,538

(22) Filed: Jan. 27, 2020

(65) Prior Publication Data
US 2020/0239563 A1    Jul. 30, 2020

Related U.S. Application Data

(60) Provisional application No. 62/797,803, filed on Jan. 28, 2019, provisional application No. 62/809,404, filed on Feb. 22, 2019.

(51) Int. Cl.
| | | |
|---|---|---|
| *C07K 16/24* | (2006.01) | |
| *A61K 39/395* | (2006.01) | |
| *A61K 9/00* | (2006.01) | |
| *A61K 39/00* | (2006.01) | |

(52) U.S. Cl.
CPC .......... *C07K 16/244* (2013.01); *A61K 9/0014* (2013.01); *A61K 9/0029* (2013.01); *A61K 39/3955* (2013.01); *A61K 2039/505* (2013.01); *A61K 2039/54* (2013.01); *A61K 2039/545* (2013.01)

(58) Field of Classification Search
None
See application file for complete search history.

(56) References Cited

U.S. PATENT DOCUMENTS

| | | |
|---|---|---|
| 2009/0137966 A1 | 5/2009 | Rueckert et al. |
| 2012/0220948 A1 | 8/2012 | Barbour |
| 2018/0243513 A1 | 8/2018 | Rolfs et al. |

FOREIGN PATENT DOCUMENTS

KR    101900427 B1    9/2018

OTHER PUBLICATIONS

Sonkoly et al, Allergy Clinical Immunology, 2006, vol. 117, No. 2, pp. 411-417.*
Cully, M. Nature Reviews Drug Discovery; online Aug. 30, 2016; doi:10.1038/nrd.2016.165.*
Nakashima et al, Experimental Dermatology; Mar. 2018; vol. 27, pp. 327-331.*
Pereira et al, European Academy of Dermatology and Venereology, 2018, vol. 32, pp. 1059-1065.*
Anonymous: "Chugai grants exclusive global license for development and marketing of nemolizumab to Galderma", Jul. 22, 2016, XP55681009, Retrieved from the Internet: URL: http://www.pharmabiz.com/ArticleDetalis.aspx?aid=96389&sid=2 (2 pages).
Galderma: "NCT03181503 Safety and Efficacy of Nemolizumab in PN Official Title: A Study to Assess the Safety and Efficacy of Nemolizumab (CD14152) in Subjects with Prurigo Nodularis (PN) Secondary IDs", Clinical Trials, Jun. 7, 2017, XP055680952, Retrieved from the Internet: URL: https://clinicaltrials.gov/ct2/history/NCT03181503?V (3 pages).
International Search Report and Written Opinion issued in PCT/IB2020/050623 dated Apr. 9, 2020 (15 pages).
International Search Report and Written Opinion on PCT Appl. Ser. No. PCT/IB2021/053601 dated May 25, 2021 (13 pages).
International Preliminary Report on Patentability on PCT Appl. Ser. No. PCT/IB2020/050623 dated Aug. 12, 2021 (8 pages).
JP Office Action on JP Appl. Ser. No. 2020-514620 dated Jul. 14, 2021.

* cited by examiner

*Primary Examiner* — Bridget E Bunner
*Assistant Examiner* — Fozia M Hamud
(74) *Attorney, Agent, or Firm* — Foley & Lardner LLP; Sunit Talapatra

(57) ABSTRACT

Disclosed herein are methods for selectively treating pruritus in a subject having chronic prurigo (CP), including prurigo nodularis (PN), pharmaceutical compositions for use in the treatment of pruritus in a subject having CP or PN, uses of nemolizumab or an equivalent thereof in the manufacture of a medicament for the treatment of pruritus in a subject having CP or PN.

25 Claims, 13 Drawing Sheets

Specification includes a Sequence Listing.

SEQUENCE LISTING

<160> NUMBER OF SEQ ID NOS: 6

<210> SEQ ID NO 1
<211> LENGTH: 662
<212> TYPE: PRT
<213> ORGANISM: Homo sapiens

<400> SEQUENCE: 1

```
Met Lys Leu Ser Pro Gln Pro Ser Cys Val Asn Leu Gly Met Met Trp
1               5                   10                  15

Thr Trp Ala Leu Trp Met Leu Pro Ser Leu Cys Lys Phe Ser Leu Ala
            20                  25                  30

Ala Leu Pro Ala Lys Pro Glu Asn Ile Ser Cys Val Tyr Tyr Tyr Arg
        35                  40                  45

Lys Asn Leu Thr Cys Thr Trp Ser Pro Gly Lys Glu Thr Ser Tyr Thr
    50                  55                  60

Gln Tyr Thr Val Lys Arg Thr Tyr Ala Phe Gly Glu Lys His Asp Asn
65                  70                  75                  80

Cys Thr Thr Asn Ser Ser Thr Ser Glu Asn Arg Ala Ser Cys Ser Phe
                85                  90                  95

Phe Leu Pro Arg Ile Thr Ile Pro Asp Asn Tyr Thr Ile Glu Val Glu
            100                 105                 110

Ala Glu Asn Gly Asp Gly Val Ile Lys Ser His Met Thr Tyr Trp Arg
        115                 120                 125

Leu Glu Asn Ile Ala Lys Thr Glu Pro Pro Lys Ile Phe Arg Val Lys
    130                 135                 140

Pro Val Leu Gly Ile Lys Arg Met Ile Gln Ile Glu Trp Ile Lys Pro
145                 150                 155                 160

Glu Leu Ala Pro Val Ser Ser Asp Leu Lys Tyr Thr Leu Arg Phe Arg
                165                 170                 175

Thr Val Asn Ser Thr Ser Trp Met Glu Val Asn Phe Ala Lys Asn Arg
            180                 185                 190

Lys Asp Lys Asn Gln Thr Tyr Asn Leu Thr Gly Leu Gln Pro Phe Thr
    195                 200                 205

Glu Tyr Val Ile Ala Leu Arg Cys Ala Val Lys Glu Ser Lys Phe Trp
210                 215                 220

Ser Asp Trp Ser Gln Glu Lys Met Gly Met Thr Glu Glu Glu Ala Pro
225                 230                 235                 240

Cys Gly Leu Glu Leu Trp Arg Val Leu Lys Pro Ala Glu Ala Asp Gly
                245                 250                 255

Arg Arg Pro Val Arg Leu Leu Trp Lys Lys Ala Arg Gly Ala Pro Val
            260                 265                 270

Leu Glu Lys Thr Leu Gly Tyr Asn Ile Trp Tyr Tyr Pro Glu Ser Asn
    275                 280                 285

Thr Asn Leu Thr Glu Thr Met Asn Thr Thr Asn Gln Gln Leu Glu Leu
290                 295                 300

His Leu Gly Gly Glu Ser Phe Trp Val Ser Met Ile Ser Tyr Asn Ser
305                 310                 315                 320

Leu Gly Lys Ser Pro Val Ala Thr Leu Arg Ile Pro Ala Ile Gln Glu
                325                 330                 335

Lys Ser Phe Gln Cys Ile Glu Val Met Gln Ala Cys Val Ala Glu Asp
            340                 345                 350

Gln Leu Val Val Lys Trp Gln Ser Ser Ala Leu Asp Val Asn Thr Trp
    355                 360                 365
```

```
Met Ile Glu Trp Phe Pro Asp Val Asp Ser Glu Pro Thr Thr Leu Ser
        370                 375                 380

Trp Glu Ser Val Ser Gln Ala Thr Asn Trp Thr Ile Gln Gln Asp Lys
385                 390                 395                 400

Leu Lys Pro Phe Trp Cys Tyr Asn Ile Ser Val Tyr Pro Met Leu His
                405                 410                 415

Asp Lys Val Gly Glu Pro Tyr Ser Ile Gln Ala Tyr Ala Lys Glu Gly
            420                 425                 430

Val Pro Ser Glu Gly Pro Glu Thr Lys Val Glu Asn Ile Gly Val Lys
        435                 440                 445

Thr Val Thr Ile Thr Trp Lys Glu Ile Pro Lys Ser Glu Arg Lys Gly
    450                 455                 460

Ile Ile Cys Asn Tyr Thr Ile Phe Tyr Gln Ala Glu Gly Gly Lys Gly
465                 470                 475                 480

Phe Ser Lys Thr Val Asn Ser Ser Ile Leu Gln Tyr Gly Leu Glu Ser
                485                 490                 495

Leu Lys Arg Lys Thr Ser Tyr Ile Val Gln Val Met Ala Ser Thr Ser
            500                 505                 510

Ala Gly Gly Thr Asn Gly Thr Ser Ile Asn Phe Lys Thr Leu Ser Phe
        515                 520                 525

Ser Val Phe Glu Ile Ile Leu Ile Thr Ser Leu Ile Gly Gly Gly Leu
    530                 535                 540

Leu Ile Leu Ile Ile Leu Thr Val Ala Tyr Gly Leu Lys Lys Pro Asn
545                 550                 555                 560

Lys Leu Thr His Leu Cys Trp Pro Thr Val Pro Asn Pro Ala Glu Ser
                565                 570                 575

Ser Ile Ala Thr Trp His Gly Asp Asp Phe Lys Asp Lys Leu Asn Leu
            580                 585                 590

Lys Glu Ser Asp Asp Ser Val Asn Thr Glu Asp Arg Ile Leu Lys Pro
        595                 600                 605

Cys Ser Thr Pro Ser Asp Lys Leu Val Ile Asp Lys Leu Val Val Asn
    610                 615                 620

Phe Gly Asn Val Leu Gln Glu Ile Phe Thr Asp Glu Ala Arg Thr Gly
625                 630                 635                 640

Gln Glu Asn Asn Leu Gly Gly Glu Lys Asn Gly Thr Arg Ile Leu Ser
                645                 650                 655

Ser Cys Pro Thr Ser Ile
            660

<210> SEQ ID NO 2
<211> LENGTH: 732
<212> TYPE: PRT
<213> ORGANISM: Homo sapiens

<400> SEQUENCE: 2

Met Met Trp Thr Trp Ala Leu Trp Met Leu Pro Ser Leu Cys Lys Phe
1               5                   10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
    50                  55                  60

His Asp Asn Cys Thr Thr Asn Ser Ser Thr Ser Glu Asn Arg Ala Ser
65                  70                  75                  80
```

```
Cys Ser Phe Phe Leu Pro Arg Ile Thr Ile Pro Asp Asn Tyr Thr Ile
                85                  90                  95
Glu Val Glu Ala Glu Asn Gly Asp Gly Val Ile Lys Ser His Met Thr
            100                 105                 110
Tyr Trp Arg Leu Glu Asn Ile Ala Lys Thr Glu Pro Pro Lys Ile Phe
        115                 120                 125
Arg Val Lys Pro Val Leu Gly Ile Lys Arg Met Ile Gln Ile Glu Trp
    130                 135                 140
Ile Lys Pro Glu Leu Ala Pro Val Ser Ser Asp Leu Lys Tyr Thr Leu
145                 150                 155                 160
Arg Phe Arg Thr Val Asn Ser Thr Ser Trp Met Glu Val Asn Phe Ala
                165                 170                 175
Lys Asn Arg Lys Asp Lys Asn Gln Thr Tyr Asn Leu Thr Gly Leu Gln
            180                 185                 190
Pro Phe Thr Glu Tyr Val Ile Ala Leu Arg Cys Ala Val Lys Glu Ser
        195                 200                 205
Lys Phe Trp Ser Asp Trp Ser Gln Glu Lys Met Gly Met Thr Glu Glu
    210                 215                 220
Glu Ala Pro Cys Gly Leu Glu Leu Trp Arg Val Leu Lys Pro Ala Glu
225                 230                 235                 240
Ala Asp Gly Arg Arg Pro Val Arg Leu Leu Trp Lys Lys Ala Arg Gly
                245                 250                 255
Ala Pro Val Leu Glu Lys Thr Leu Gly Tyr Asn Ile Trp Tyr Tyr Pro
            260                 265                 270
Glu Ser Asn Thr Asn Leu Thr Glu Thr Met Asn Thr Thr Asn Gln Gln
        275                 280                 285
Leu Glu Leu His Leu Gly Gly Glu Ser Phe Trp Val Ser Met Ile Ser
    290                 295                 300
Tyr Asn Ser Leu Gly Lys Ser Pro Val Ala Thr Leu Arg Ile Pro Ala
305                 310                 315                 320
Ile Gln Glu Lys Ser Phe Gln Cys Ile Glu Val Met Gln Ala Cys Val
                325                 330                 335
Ala Glu Asp Gln Leu Val Val Lys Trp Gln Ser Ser Ala Leu Asp Val
            340                 345                 350
Asn Thr Trp Met Ile Glu Trp Phe Pro Asp Val Asp Ser Glu Pro Thr
        355                 360                 365
Thr Leu Ser Trp Glu Ser Val Ser Gln Ala Thr Asn Trp Thr Ile Gln
    370                 375                 380
Gln Asp Lys Leu Lys Pro Phe Trp Cys Tyr Asn Ile Ser Val Tyr Pro
385                 390                 395                 400
Met Leu His Asp Lys Val Gly Glu Pro Tyr Ser Ile Gln Ala Tyr Ala
                405                 410                 415
Lys Glu Gly Val Pro Ser Glu Gly Pro Glu Thr Lys Val Glu Asn Ile
            420                 425                 430
Gly Val Lys Thr Val Thr Ile Thr Trp Lys Glu Ile Pro Lys Ser Glu
        435                 440                 445
Arg Lys Gly Ile Ile Cys Asn Tyr Thr Ile Phe Tyr Gln Ala Glu Gly
    450                 455                 460
Gly Lys Gly Phe Ser Lys Thr Val Asn Ser Ser Ile Leu Gln Tyr Gly
465                 470                 475                 480
Leu Glu Ser Leu Lys Arg Lys Thr Ser Tyr Ile Val Gln Val Met Ala
                485                 490                 495
```

Ser Thr Ser Ala Gly Gly Thr Asn Gly Thr Ser Ile Asn Phe Lys Thr
            500                 505                 510

Leu Ser Phe Ser Val Phe Glu Ile Ile Leu Ile Thr Ser Leu Ile Gly
        515                 520                 525

Gly Gly Leu Leu Ile Leu Ile Ile Leu Thr Val Ala Tyr Gly Leu Lys
    530                 535                 540

Lys Pro Asn Lys Leu Thr His Leu Cys Trp Pro Thr Val Pro Asn Pro
545                 550                 555                 560

Ala Glu Ser Ser Ile Ala Thr Trp His Gly Asp Asp Phe Lys Asp Lys
                565                 570                 575

Leu Asn Leu Lys Glu Ser Asp Asp Ser Val Asn Thr Glu Asp Arg Ile
            580                 585                 590

Leu Lys Pro Cys Ser Thr Pro Ser Asp Lys Leu Val Ile Asp Lys Leu
        595                 600                 605

Val Val Asn Phe Gly Asn Val Leu Gln Glu Ile Phe Thr Asp Glu Ala
    610                 615                 620

Arg Thr Gly Gln Glu Asn Asn Leu Gly Gly Lys Asn Gly Tyr Val
625                 630                 635                 640

Thr Cys Pro Phe Arg Pro Asp Cys Pro Leu Gly Lys Ser Phe Glu Glu
                645                 650                 655

Leu Pro Val Ser Pro Glu Ile Pro Pro Arg Lys Ser Gln Tyr Leu Arg
            660                 665                 670

Ser Arg Met Pro Glu Gly Thr Arg Pro Glu Ala Lys Glu Gln Leu Leu
        675                 680                 685

Phe Ser Gly Gln Ser Leu Val Pro Asp His Leu Cys Glu Glu Gly Ala
    690                 695                 700

Pro Asn Pro Tyr Leu Lys Asn Ser Val Thr Ala Arg Glu Phe Leu Val
705                 710                 715                 720

Ser Glu Lys Leu Pro Glu His Thr Lys Gly Glu Val
            725                 730

<210> SEQ ID NO 3
<211> LENGTH: 716
<212> TYPE: PRT
<213> ORGANISM: Mus musculus

<400> SEQUENCE: 3

Met Trp Thr Leu Ala Leu Trp Ala Phe Ser Phe Leu Cys Lys Phe Ser
1               5                   10                  15

Leu Ala Val Leu Pro Thr Lys Pro Glu Asn Ile Ser Cys Val Phe Tyr
            20                  25                  30

Phe Asp Arg Asn Leu Thr Cys Thr Trp Arg Pro Glu Lys Glu Thr Asn
        35                  40                  45

Asp Thr Ser Tyr Ile Val Thr Leu Thr Tyr Ser Tyr Gly Lys Ser Asn
    50                  55                  60

Tyr Ser Asp Asn Ala Thr Glu Ala Ser Tyr Ser Phe Pro Arg Ser Cys
65                  70                  75                  80

Ala Met Pro Pro Asp Ile Cys Ser Val Glu Val Gln Ala Gln Asn Gly
                85                  90                  95

Asp Gly Lys Val Lys Ser Asp Ile Thr Tyr Trp His Leu Ile Ser Ile
            100                 105                 110

Ala Lys Thr Glu Pro Pro Ile Ile Leu Ser Val Asn Pro Ile Cys Asn
        115                 120                 125

Arg Met Phe Gln Ile Gln Trp Lys Pro Arg Glu Lys Thr Arg Gly Phe
    130                 135                 140

```
Pro Leu Val Cys Met Leu Arg Phe Arg Thr Val Asn Ser Ser Arg Trp
145                 150                 155                 160

Thr Glu Val Asn Phe Glu Asn Cys Lys Gln Val Cys Asn Leu Thr Gly
            165                 170                 175

Leu Gln Ala Phe Thr Glu Tyr Val Leu Ala Leu Arg Phe Arg Phe Asn
        180                 185                 190

Asp Ser Arg Tyr Trp Ser Lys Trp Ser Lys Glu Glu Thr Arg Val Thr
    195                 200                 205

Met Glu Glu Val Pro His Val Leu Asp Leu Trp Arg Ile Leu Glu Pro
210                 215                 220

Ala Asp Met Asn Gly Asp Arg Lys Val Arg Leu Leu Trp Lys Lys Ala
225                 230                 235                 240

Arg Gly Ala Pro Val Leu Glu Lys Thr Phe Gly Tyr His Ile Gln Tyr
                245                 250                 255

Phe Ala Glu Asn Ser Thr Asn Leu Thr Glu Ile Asn Asn Ile Thr Thr
                260                 265                 270

Gln Gln Tyr Glu Leu Leu Leu Met Ser Gln Ala His Ser Val Ser Val
            275                 280                 285

Thr Ser Phe Asn Ser Leu Gly Lys Ser Gln Glu Ala Ile Leu Arg Ile
290                 295                 300

Pro Asp Val His Glu Lys Thr Phe Gln Tyr Ile Lys Ser Met Lys Ala
305                 310                 315                 320

Tyr Ile Ala Glu Pro Leu Leu Val Val Asn Trp Gln Ser Ser Ile Pro
                325                 330                 335

Ala Val Asp Thr Trp Ile Val Glu Trp Leu Pro Glu Ala Ala Met Ser
                340                 345                 350

Lys Phe Pro Ala Leu Ser Trp Glu Ser Val Ser Gln Val Thr Asn Trp
                355                 360                 365

Thr Ile Glu Gln Asp Lys Leu Lys Pro Phe Thr Cys Tyr Asn Ile Ser
370                 375                 380

Val Tyr Pro Val Leu Gly His Arg Val Gly Glu Pro Tyr Ser Ile Gln
385                 390                 395                 400

Ala Tyr Ala Lys Glu Gly Thr Pro Leu Lys Gly Pro Glu Thr Arg Val
                405                 410                 415

Glu Asn Ile Gly Leu Arg Thr Ala Thr Ile Thr Trp Lys Glu Ile Pro
                420                 425                 430

Lys Ser Ala Arg Asn Gly Phe Ile Asn Asn Tyr Thr Val Phe Tyr Gln
                435                 440                 445

Ala Glu Gly Gly Lys Glu Leu Ser Lys Thr Val Asn Ser His Ala Leu
                450                 455                 460

Gln Cys Asp Leu Glu Ser Leu Thr Arg Arg Thr Ser Tyr Thr Val Trp
465                 470                 475                 480

Val Met Ala Ser Thr Arg Ala Gly Gly Thr Asn Gly Val Arg Ile Asn
                485                 490                 495

Phe Lys Thr Leu Ser Ile Ser Val Phe Glu Ile Val Leu Leu Thr Ser
                500                 505                 510

Leu Val Gly Gly Gly Leu Leu Leu Ser Ile Lys Thr Val Thr Phe
                515                 520                 525

Gly Leu Arg Lys Pro Asn Arg Leu Thr Pro Leu Cys Cys Pro Asp Val
        530                 535                 540

Pro Asn Pro Ala Glu Ser Ser Leu Ala Thr Trp Leu Gly Asp Gly Phe
545                 550                 555                 560
```

```
Lys Lys Ser Asn Met Lys Glu Thr Gly Asn Ser Gly Asp Thr Glu Asp
                565             570             575

Val Val Leu Lys Pro Cys Pro Val Pro Ala Asp Leu Ile Asp Lys Leu
            580             585             590

Val Val Asn Phe Glu Asn Phe Leu Glu Val Val Leu Thr Glu Glu Ala
        595             600             605

Gly Lys Gly Gln Ala Ser Ile Leu Gly Gly Glu Ala Asn Glu Tyr Val
    610             615             620

Thr Ser Pro Ser Arg Pro Asp Gly Pro Pro Gly Lys Ser Phe Lys Glu
625             630             635             640

Pro Ser Val Leu Thr Glu Val Ala Ser Glu Asp Ser His Ser Thr Cys
            645             650             655

Ser Arg Met Ala Asp Glu Ala Tyr Ser Glu Leu Ala Arg Gln Pro Ser
            660             665             670

Ser Ser Cys Gln Ser Pro Gly Leu Ser Pro Arg Glu Asp Gln Ala
            675             680             685

Gln Asn Pro Tyr Leu Lys Asn Ser Val Thr Thr Arg Glu Phe Leu Val
        690             695             700

His Glu Asn Ile Pro Glu His Ser Lys Gly Glu Val
705             710             715
```

<210> SEQ ID NO 4
<211> LENGTH: 735
<212> TYPE: PRT
<213> ORGANISM: Macaca fascicularis

<400> SEQUENCE: 4

```
Met Met Trp Thr Trp Ala Leu Trp Met Phe Pro Leu Leu Cys Lys Phe
1               5                   10                  15

Gly Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Ala Lys Arg Thr Tyr Ala Phe Gly Lys Lys
    50                  55                  60

His Asp Asn Cys Thr Thr Ser Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser Asp Met Thr
            100                 105                 110

Cys Trp Arg Leu Glu Asp Ile Ala Lys Thr Glu Pro Pro Glu Ile Phe
        115                 120                 125

Ser Val Lys Pro Val Leu Gly Ile Lys Arg Met Ile Arg Ile Glu Trp
    130                 135                 140

Ile Lys Pro Glu Leu Ala Pro Val Ser Ser Asp Leu Lys Tyr Ala Leu
145                 150                 155                 160

Arg Phe Arg Thr Val Asn Ser Thr Ser Trp Met Glu Val Asn Phe Ala
                165                 170                 175

Lys Asn Arg Lys Asp Thr Asn Gln Thr Tyr Asn Leu Met Gly Leu Gln
            180                 185                 190

Ala Phe Thr Glu Tyr Val Val Ala Leu Arg Cys Ala Val Lys Glu Ser
        195                 200                 205

Lys Phe Trp Ser Asp Trp Ser Gln Glu Lys Met Gly Met Thr Glu Glu
    210                 215                 220
```

```
Glu Ala Pro Cys Gly Leu Glu Leu Trp Arg Val Leu Lys Pro Thr Glu
225                 230                 235                 240

Val Asp Gly Arg Arg Pro Val Arg Leu Leu Trp Lys Lys Ala Arg Gly
            245                 250                 255

Ala Pro Val Leu Glu Lys Thr Leu Gly Tyr Asn Ile Trp Tyr Phe Pro
                260                 265                 270

Glu Asn Asn Thr Asn Leu Thr Glu Thr Val Asn Thr Thr Asn Gln Gln
            275                 280                 285

Leu Glu Leu His Leu Gly Gly Glu Ser Tyr Trp Val Ser Met Ile Ser
        290                 295                 300

Tyr Asn Ser Leu Gly Lys Ser Pro Val Thr Thr Leu Arg Ile Pro Ala
305                 310                 315                 320

Ile Gln Glu Lys Ser Phe Arg Cys Ile Glu Val Met Gln Ala Cys Leu
                325                 330                 335

Ala Glu Asp Gln Leu Val Val Lys Trp Gln Ser Ser Ala Leu Asp Val
            340                 345                 350

Asn Thr Trp Met Ile Glu Trp Phe Pro Asp Met Asp Ser Glu His Pro
        355                 360                 365

Thr Leu Ser Trp Glu Ser Val Ser Gln Ala Thr Asn Trp Thr Ile Gln
370                 375                 380

Gln Asp Lys Leu Lys Pro Phe Trp Cys Tyr Asn Ile Ser Val Tyr Pro
385                 390                 395                 400

Met Leu His Asp Lys Val Gly Glu Pro Tyr Ser Ile Gln Ala Tyr Ala
                405                 410                 415

Lys Glu Gly Ile Pro Ser Lys Gly Pro Glu Thr Lys Val Glu Asn Ile
                420                 425                 430

Gly Val Lys Thr Val Thr Ile Thr Trp Lys Glu Ile Pro Lys Ser Glu
        435                 440                 445

Arg Lys Gly Ile Ile Cys Asn Tyr Thr Ile Phe Tyr Gln Ala Glu Gly
450                 455                 460

Gly Lys Gly Phe Ser Lys Thr Val Asn Ser Ser Ile Leu Gln Tyr Gly
465                 470                 475                 480

Leu Glu Ser Leu Lys Arg Lys Thr Ser Tyr Thr Val Arg Val Met Ala
                485                 490                 495

Ser Thr Ser Ala Gly Gly Ile Asn Gly Thr Ser Ile Asn Phe Lys Thr
            500                 505                 510

Leu Ser Phe Ser Val Phe Glu Ile Ile Leu Ile Thr Ser Leu Ile Gly
        515                 520                 525

Gly Gly Leu Leu Ile Leu Ile Ile Leu Thr Val Ala Tyr Gly Leu Lys
    530                 535                 540

Lys Pro Asn Lys Leu Thr His Leu Cys Trp Pro Ser Val Pro Asn Pro
545                 550                 555                 560

Ala Glu Ser Ser Ile Ala Thr Trp Arg Gly Asp Asp Phe Lys Asp Lys
                565                 570                 575

Leu Asn Leu Lys Glu Ser Asp Asp Ser Val Asn Thr Glu Asp Arg Ile
                580                 585                 590

Leu Lys Pro Cys Ser Thr Pro Ser Asp Lys Leu Val Ile Asp Lys Ser
                595                 600                 605

Val Val Asn Phe Gly Asn Val Leu Gln Glu Met Phe Thr Asp Glu Ala
            610                 615                 620

Arg Thr Gly Gln Glu Asn Asn Leu Gly Gly Glu Lys Asn Glu Tyr Val
625                 630                 635                 640
```

```
Thr His Pro Phe Arg Ala Asp Cys Pro Leu Gly Lys Ser Phe Glu Glu
                645                 650                 655

Leu Pro Val Ser Pro Glu Ile Pro Pro Arg Lys Ser Gln Tyr Leu Arg
            660                 665                 670

Ser Arg Met Pro Glu Gly Thr Cys Leu Glu Ala Glu Glu Gln Leu Leu
        675                 680                 685

Val Ser Gly Gln Ser Leu Glu Ser Leu Ala Pro Asp His Val Arg Glu
    690                 695                 700

Ala Ala Ala Pro Asn Pro Tyr Leu Lys Asn Ser Val Thr Thr Arg Glu
705                 710                 715                 720

Phe Leu Val Ser Gln Lys Leu Pro Glu His Thr Lys Gly Glu Val
                725                 730                 735

<210> SEQ ID NO 5
<211> LENGTH: 445
<212> TYPE: PRT
<213> ORGANISM: Artificial Sequence
<220> FEATURE:
<223> OTHER INFORMATION: Nemolizumab heavy chain amino acid sequence

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Asp Tyr Asn Pro Gln Phe
    50                  55                  60

Gln Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270
```

```
Val Gln Phe Asn Trp Tyr Val Asp Gly Val Glu Val His Asn Ala Lys
            275                 280                 285

Thr Lys Pro Arg Glu Glu Gln Phe Asn Ser Thr Phe Arg Val Val Ser
            290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro
            435                 440                 445

<210> SEQ ID NO 6
<211> LENGTH: 214
<212> TYPE: PRT
<213> ORGANISM: Artificial Sequence
<220> FEATURE:
<223> OTHER INFORMATION: Nemolizumab light chain amino acid sequence

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Tyr Ser Phe
            20                  25                  30

Val Ala Trp Tyr Gln Gln Lys Pro Gly Lys Ala Pro Lys Leu Leu Ile
            35                  40                  45

Tyr Asn Ala Gln Thr Glu Ala Gln Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Asp Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

-continued

```
Ala Cys Glu Val Thr His Gln Gly Leu Ser Ser Pro Val Thr Lys Ser
        195                 200                 205

Phe Asn Arg Gly Glu Cys
    210
```

TREATMENT OF SKIN LESIONS AND PRURITUS IN PRURIGO NODULARIS PATIENTS

RELATED APPLICATIONS

This application claims priority under 35 U.S.C. § 119(e) to U.S. Provisional Application No. 62/797,803 filed Jan. 28, 2019, and U.S. Provisional Application No. 62/809,404 filed Feb. 22, 2019, the entire contents of which are incorporated herein by reference.

SEQUENCE LISTING

The instant application contains a Sequence Listing which has been filed electronically in ASCII format and is hereby incorporated by reference in its entirety. Said ASCII copy, created on Jan. 27, 2020, is named 105153-3002_SEQ_LST.txt and is 30 kilobytes in size.

FIELD

Described herein are methods for treating skin lesions and pruritus of a subject having chronic prurigo (CP), including prurigo nodularis (PN), pharmaceutical compositions for use in the treatment of skin lesions and pruritus in a subject having CP, uses of nemolizumab or an equivalent thereof in the manufacture of a medicament for the treatment of skin lesions and pruritus in a subject having CP.

BACKGROUND

The following discussion is provided to aid the reader in understanding the disclosure and is not admitted to describe or constitute prior art thereto.

Chronic prurigo (CP) is a skin disease due to neuronal sensitization to itch and development of an itch-scratch cycle. Prurigo nodularis (PN), a subtype of CP, and is a skin disease that causes hard, itchy lumps (nodules) to form on the skin. The itching (pruritus) can be intense, causing people to scratch themselves to the point of bleeding or pain. Scratching can cause more skin lesions to appear. The itching is worsened by heat, sweating, or irritation from clothing. In some cases, people with PN have a history of other diseases including eczema (atopic dermatitis), diabetes, lymphoma, HIV infection, severe anemia, or kidney disease.

The exact cause of CP or PN is unknown. Although scratching is known to cause more nodules to appear, it is unclear what causes the itching to develop in the first place. Diagnosis of the disease is based on observing signs such as extremely itchy skin with the formation of nodules. In some cases, a skin biopsy is used to confirm the diagnosis. Currently treatment may include corticosteroid creams, oral medications, cryotherapy, or photochemotherapy.

There remains a need to develop novel therapeutic regimes to treat patients with PN, particularly those suffering from chronic pruritus.

SUMMARY

Provided herein are methods for treating skin lesions and pruritus in a subject having chronic prurigo (CP) including prurigo nodularis (PN), pharmaceutical compositions for use in the treatment of skin lesions and pruritus in a subject having CP including PN, uses of nemolizumab or an equivalent thereof in the manufacture of a medicament for the treatment of skin lesions and pruritus in a subject having CP including PN.

In accordance with some embodiments, there are provided methods of treating skin lesions and pruritus in a subject having CP, the method comprising, consisting of, or consisting essentially of administering an effective amount of nemolizumab or an equivalent thereof to the subject.

In some embodiments of the methods, the subject has prurigo nodularis (PN). In some embodiments of the methods, the subject has been diagnosed of PN for at least about 6 months. In particular embodiments of the methods, the subject has at least about 20 nodules on his/her body with a bilateral distribution. In particular embodiments of the methods, the subject has prurigo lesions on upper limbs, with or without lesions on the trunk or lower limbs. In particular embodiments of the methods, the pruritus has been assigned a score of at least 4, while in some embodiments the pruritus has been assigned a score of at least 7 on the Numerical Rating Scale (NRS). In particular embodiments of the methods, the mean of the worst daily intensity of the NRS score is at least 7 over the previous 3 days. In other particular embodiments of the methods, the mean of the worst daily intensity of the NRS score is at least 7 over the previous week.

In some embodiments of the methods, the subject does not have atopic dermatitis. In some embodiments of the methods, the subject does not have chronic pruritus resulting from a condition other than PN, such as scabies, insect bite, lichen simplex chronicus, psoriasis, acne, folliculitis, habitual picking, lymphomatoid papulosis, chronic actinic dermatitis, dermatitis herpetiformis, sporotrichosis, bullous disease. In some embodiments of the methods, the subject does not have neuropathic or psychogenic pruritus, such as notalgia paresthetica, brachioradial pruritus, dilutional parasitosis, pathomimia.

In some embodiments of the methods, the effective amount of nemolizumab or the equivalent thereof ranges from about 0.01 mg/kg to about 0.1 mg/kg, about 0.1 mg/kg to about 0.5 mg/kg, about 0.5 mg/kg to about 1.5 mg/kg, about 1.5 mg/kg to about 2.5 mg/kg, or about 2.5 mg/kg to about 10 mg/kg. In particular embodiments, the effective amount of nemolizumab or the equivalent thereof is about 0.1 mg/kg, about 0.5 mg/kg, about 1 mg/kg, about 1.5 mg/kg, about 2 mg/kg, or about 2.5 mg/kg. In particular embodiments, the effective amount of nemolizumab or the equivalent thereof is a 40 mg flat dose. In other particular embodiments, the effective amount of nemolizumab or equivalent thereof is 30 mg with a 60 mg loading dose. In other particular embodiments, the effective amount of nemolizumab or the equivalent thereof is 6 60 mg flat dose, administered once every 4 weeks. In some embodiments of the methods, the nemolizumab or the equivalent thereof is administered by a topical or parenteral route. In some embodiments of the methods, the nemolizumab or the equivalent thereof is administered subcutaneously. In some embodiments, the nemolizumab or the equivalent thereof is administered once per week, once every two weeks, once every three weeks, once every four weeks, once every five weeks, once every six weeks, once every seven weeks, or once every eight weeks. In certain embodiments, the nemolizumab is administered over a period of at least 2 weeks, 3 weeks, 1 month, 1.5 months, 2 months, 3 months, 4 months, 5 months, 6 months or longer.

In accordance with some embodiments, there are provided pharmaceutical compositions for use in the treatment of skin lesion and pruritus in a subject having chronic prurigo (CP), the composition comprising, consisting of, or consisting essentially of nemolizumab or an equivalent thereof.

In some embodiments of the pharmaceutical compositions, the subject has prurigo nodularis (PN). In some embodiments of the compositions, the subject has been diagnosed of PN for at least about 6 months. In particular embodiments of the compositions, the subject has at least about 20 nodules on his/her body with a bilateral distribution. In particular embodiments of the compositions, the subject has prurigo lesions on upper limbs, with or without lesions on the trunk or lower limbs. In particular embodiments of the compositions, the pruritus has been assigned a score of at least 4, while in some embodiments the pruritus has been assigned a score of at least 7 on the Numerical Rating Scale (NRS). In particular embodiments of the compositions, the mean of the worst daily intensity of the NRS score is at least 7 over the previous 3 days. In other particular embodiments of the compositions, the mean of the worst daily intensity of the NRS score is at least 7 over the previous week.

In some embodiments of the pharmaceutical compositions, the subject does not have atopic dermatitis. In some embodiments of the compositions, the subject does not have chronic pruritus resulting from a condition other than PN, such as scabies, insect bite, lichen simplex chronicus, psoriasis, acne, folliculitis, habitual picking, lymphomatoid papulosis, chronic actinic dermatitis, dermatitis herpetiformis, sporotrichosis, bullous disease. In some embodiments of the compositions, the subject does not have neuropathic or psychogenic pruritus, such as notalgia paresthetica, brachioradial pruritus, dilutional parasitosis, pathomimia.

In some embodiments, the pharmaceutical composition further comprises a carrier. In some embodiments, the carrier is a pharmaceutically acceptable carrier.

In some embodiments of the pharmaceutical compositions, the nemolizumab or equivalent thereof is administered according to a flat dosing regimen, while in some embodiments the nemolizumab or equivalent thereof is administered according to a loading dose regimen, in which the loading dose may be higher than the subsequent serial doses (e.g., a 60 mg loading dose followed by 30 mg serial doses).

In some embodiments of the pharmaceutical compositions, the nemolizumab or equivalent thereof is administered at a dose of about 0.01 mg/kg to about 0.1 mg/kg, about 0.1 mg/kg to about 0.5 mg/kg, about 0.5 mg/kg to about 1.5 mg/kg, about 1.5 mg/kg to about 2.5 mg/kg, or about 2.5 mg/kg to about 10 mg/kg. while in some embodiments, the nemolizumab or equivalent thereof is administered at a dose of about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg of nemolizumab or the equivalent thereof.

In accordance with some embodiments, there are provided uses of nemolizumab or an equivalent thereof in the manufacture of a medicament for the treatment of pruritus in a subject having PN.

In some embodiments of the uses, the pruritus is moderate to severe. In some embodiments of the uses, the subject has been diagnosed of PN for at least 6 months. In particular embodiments of the uses, the subject has at least 20 nodules on his/her body with a bilateral distribution. In particular embodiments of the uses, the subject has prurigo lesions on upper limbs, with or without lesions on the trunk or lower limbs. In particular embodiments of the uses, pruritus has been assigned a score of at least 4, while in some embodiments the pruritus has been assigned a score of at least 7 on the Numerical Rating Scale (NRS). In particular embodiments of the uses, the mean of the worst daily intensity of the NRS score is at least 7 over the previous 3 days. In other particular embodiments of the uses, the mean of the worst daily intensity of the NRS score is at least 7 over the previous week.

In some embodiments of the uses, the subject does not have atopic dermatitis. In some embodiments of the uses, the subject does not have chronic pruritus resulting from a condition other than PN, such as scabies, insect bite, lichen simplex chronicus, psoriasis, acne, folliculitis, habitual picking, lymphomatoid papulosis, chronic actinic dermatitis, dermatitis herpetiformis, sporotrichosis, bullous disease. In some embodiments of the uses, the subject does not have neuropathic or psychogenic pruritus, such as notalgia paresthetica, brachioradial pruritus, dilutional parasitosis, pathomimia.

In some embodiments of the uses, the nemolizumab or equivalent thereof is administered according to a flat dosing regimen, while in some embodiments the nemolizumab or equivalent thereof is administered according to a loading dose regimen, in which the loading dose may be higher than the subsequent serial doses (e.g., a 60 mg loading dose followed by 30 mg serial doses).

In some embodiments of the uses, the nemolizumab or equivalent thereof is administered at a dose of about 0.01 mg/kg to about 0.1 mg/kg, about 0.1 mg/kg to about 0.5 mg/kg, about 0.5 mg/kg to about 1.5 mg/kg, about 1.5 mg/kg to about 2.5 mg/kg, or about 2.5 mg/kg to about 10 mg/kg. while in some embodiments, the nemolizumab or equivalent thereof is administered at a dose of about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg of nemolizumab or the equivalent thereof.

DETAILED DESCRIPTION

Figure 1:
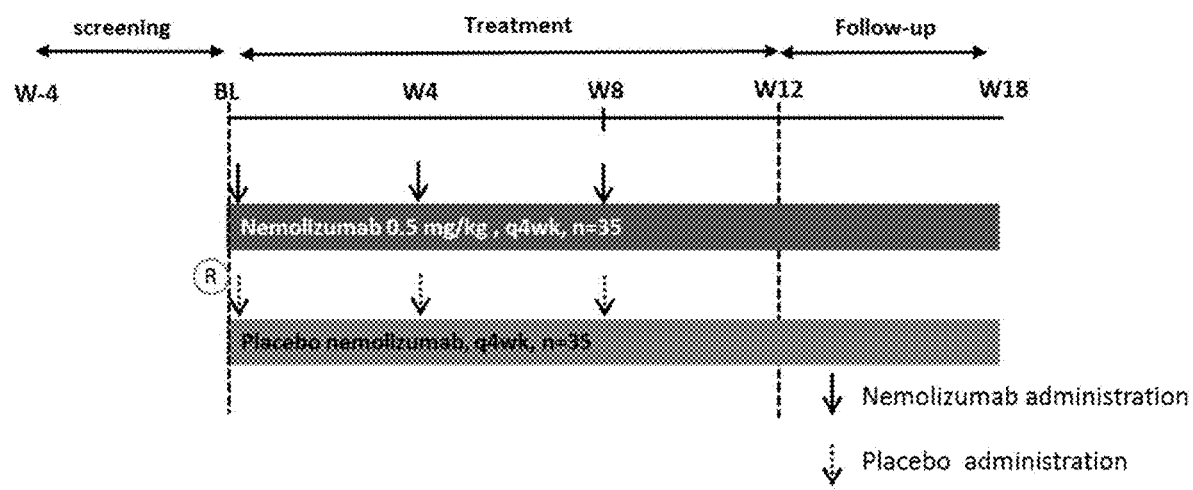
FIG. 1 Overview of the clinical study of treating pruritus in patient having prurigo nodularis (PN) with nemolizumab. A multi-center (20 sites in EU & US), randomized, double-blinded, placebo-controlled, parallel group study was conducted with approximately 70 randomized patients in 2 arms (35 per arm) were conducted, and stratified on background of atopy. Enrolled patients received nemolizumab or placebo at a dose of 0.5 mg/kg every 4 weeks from baseline to Week 8.

Embodiments according to the present disclosure will be described more fully hereinafter. Aspects of the disclosure may, however, be embodied in different forms and should not be construed as limited to the embodiments set forth herein. Rather, these embodiments are provided so that this disclosure will be thorough and complete, and will fully convey the scope of the invention to those skilled in the art. The terminology used in the description herein is for the purpose of describing particular embodiments only and is not intended to be limiting.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. While not explicitly defined below, such terms should be interpreted according to their common meaning.

The terminology used in the description herein is for the purpose of describing particular embodiments only and is not intended to be limiting of the invention. All publications, patent applications, patents and other references mentioned herein are incorporated by reference in their entirety.

Unless the context indicates otherwise, it is specifically intended that the various features of the invention described herein can be used in any combination. Moreover, the disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless explicitly indicated otherwise, all specified embodiments, features, and terms intend to include both the recited embodiment, feature, or term and biological equivalents thereof.

DEFINITIONS

As used herein, the singular forms "a," "an," and "the" designate both the singular and the plural, unless expressly stated to designate the singular only.

It is to be understood, although not always explicitly stated, that all numerical designations are preceded by the term "about." The term "about" means that the number comprehended is not limited to the exact number set forth herein, and is intended to refer to numbers substantially around the recited number while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 15%, 10%, 5%, 1%, or 0.1% of the particular term.

Also as used herein, "and/or" refers to and encompasses any and all possible combinations of one or more of the associated listed items, as well as the lack of combinations when interpreted in the alternative ("or").

The terms "administer," "administration," or "administering" as used herein refer to (1) providing, giving, dosing and/or prescribing, such as by either a health professional or his or her authorized agent or under his direction, and (2) putting into, taking or consuming, such as by a health professional or the subject. Administration shall include without limitation, administration by oral, parenteral (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration. The invention is not limited by the route of administration, the formulation or dosing schedule.

The terms "treat", "treating" or "treatment", as used herein, include alleviating, abating or ameliorating PN, pruritus, or one or more symptoms thereof, whether or not PN and/or pruritus is considered to be "cured" or "healed" and whether or not all symptoms are resolved. The terms also include reducing or preventing progression of PN and/or pruritus or one or more symptoms thereof, impeding or preventing an underlying mechanism of PN and/or pruritus or one or more symptoms thereof, and achieving any therapeutic and/or prophylactic benefit.

Interleukin 31 receptor subunit alpha ("IL-31RA," also known as NR10, glm-r, and GPL) is a protein that forms a heterodimer with oncostatin M receptor (OSMR) and functions as an IL-31 receptor. There are multiple known splicing variants of human-derived IL-31RA (WO 00/075314):

NR10.1 consists of 662 amino acids and contains a transmembrane domain. NR10.2 is a soluble receptor-like protein consisting of 252 amino acids without the transmembrane domain. Meanwhile, known IL-31RA splicing variants that function as transmembrane receptor proteins include NR10.3 and IL-31RAv3. Preferred IL-31RA variants include NR10.3 (also referred to as ILRAv4 (Nat Immunol 5, 752-60, 2004) and IL-31RAv3. NR10.3 (IL31RAv4) consists of 662 amino acids (WO 00/075314; Nat Immunol 5, 752-60, 2004) and IL31RAv3 consists of 732 amino acids (GenBank Accession No: NM-139017).

The amino acid sequence of IL31RAv4 is:

(SEQ ID NO: 1)
MKLSPQPSCVNLGMMWTWALWMLPSLCKFSLAALPAKPENISCVYYYR

KNLTCTWSPGKETSYTQYTVKRTYAFGEKHDNCTTNSSTSENRASCSF

FLPRITIPDNYTIEVEAENGDGVIKSHMTYWRLENIAKTEPPKIFRVK

PVLGIKRMIQIEWIKPELAPVSSDLKYTLRFRTVNSTSWMEVNFAKNR

KDKNQTYNLTGLQPFTEYVIALRCAVKESKFWSDWSQEKMGMTEEEAP

CGLELWRVLKPAEADGRRPVRLLWKKARGAPVLEKTLGYNIWYYPESN

TNLTETMNTTNQQLELHLGGESFWVSMISYNSLGKSPVATLRIPAIQE

KSFQCIEVMQACVAEDQLVVKWQSSALDVNTWMIEWFPDVDSEPTTLS

WESVSQATNWTIQQDKLKPFWCYNISVYPMLHDKVGEPYSIQAYAKEG

VPSEGPETKVENIGVKTVTITWKEIPKSERKGIICNYTIFYQAEGGKG

FSKTVNSSILQYGLESLKRKTSYIVQVMASTSAGGTNGTSINFKTLSF

SVFEIILITSLIGGGLLILIILTVAYGLKKPNKLTHLCWPTVPNPAES

SIATWHGDDFKDKLNLKESDDSVNTEDRILKPCSTPSDKLVIDKLVVN

FGNVLQEIFTDEARTGQENNLGGEKNGTRILSSCPTSI

The amino acid sequence of IL31RAv3 is:

(SEQ ID NO: 2)
MMWTWALWMLPSLCKFSLAALPAKPENISCVYYYRKNLTCTWSPGKET

SYTQYTVKRTYAFGEKHDNCTTNSSTSENRASCSFFLPRITIPDNYTI

EVEAENGDGVIKSHMTYWRLENIAKTEPPKIFRVKPVLGIKRMIQIEW

IKPELAPVSSDLKYTLRFRTVNSTSWMEVNFAKNRKDKNQTYNLTGLQ

PFTEYVIALRCAVKESKFWSDWSQEKMGMTEEEAPCGLELWRVLKPAE

ADGRRPVRLLWKKARGAPVLEKTLGYNIWYYPESNTNLTETMNTTNQQ

LELHLGGESFWVSMISYNSLGKSPVATLRIPAIQEKSFQCIEVMQACV

AEDQLVVKWQSSALDVNTWMIEWFPDVDSEPTTLSWESVSQATNWTIQ

QDKLKPFWCYNISVYPMLHDKVGEPYSIQAYAKEGVPSEGPETKVENI

GVKTVTITWKEIPKSERKGIICNYTIFYQAEGGKGFSKTVNSSILQYG

LESLKRKTSYIVQVMASTSAGGTNGTSINFKTLSFSVFEIILITSLIG

GGLLILIILTVAYGLKKPNKLTHLCWPTVPNPAESSIATWHGDDFKDK

LNLKESDDSVNTEDRILKPCSTPSDKLVIDKLVVNFGNVLQEIFTDEA

RTGQENNLGGEKNGYVTCPFRPDCPLGKSFEELPVSPEIPPRKSQYLR

SRMPEGTRPEAKEQLLFSGQSLVPDHLCEEGAPNPYLKNSVTAREFLV

SEKLPEHTKGEV

Mouse-derived IL-31RA includes proteins comprising the amino acid sequence:

(SEQ ID NO: 3)
MWTLALWAFSFLCKFSLAVLPTKPENISCVFYFDRNLTCTWRPEKETN

DTSYIVTLTYSYGKSNYSDNATEASYSFPRSCAMPPDICSVEVQAQNG

DGKVKSDITYWHLISIAKTEPPIILSVNPICNRMFQIQWKPREKTRGF

PLVCMLRFRTVNSSRWTEVNFENCKQVCNLTGLQAFTEYVLALRFRFN

DSRYWSKWSKEETRVTMEEVPHVLDLWRILEPADMNGDRKVRLLWKKA

RGAPVLEKTFGYHIQYFAENSTNLTEINNITTQQYELLLMSQAHSVSV

TSFNSLGKSQEAILRIPDVHEKTFQYIKSMKAYIAEPLLVVNWQSSIP

AVDTWIVEWLPEAAMSKFPALSWESVSQVTNWTIEQDKLKPFTCYNIS

VYPVLGHRVGEPYSIQAYAKEGTPLKGPETRVENIGLRTATITWKEIP

KSARNGFINNYTVFYQAEGGKELSKTVNSHALQCDLESLTRRTSYTVW

VMASTRAGGTNGVRINFKTLSISVFEIVLLTSLVGGGLLLLSIKTVTF

GLRKPNRLTPLCCPDVPNPAESSLATWLGDGEKKSNMKETGNSGDTED

VVLKPCPVPADLIDKLVVNFENFLEVVLTEEAGKGQASILGGEANEYV

TSPSRPDGPPGKSFKEPSVLTEVASEDSHSTCSRMADEAYSELARQPS

SSCQSPGLSPPREDQAQNPYLKNSVTTREFLVHENIPEHSKGEV

Cynomolgus monkey-derived IL-31RA includes proteins comprising the amino acid sequence:

(SEQ ID NO: 4)
MMWTWALWMFPLLCKFGLAALPAKPENISCVYYYRKNLTCTWSPGKET

SYTQYTAKRTYAFGKKHDNCTTSSSTSENRASCSFFLPRITIPDNYTI

EVEAENGDGVIKSDMTCWRLEDIAKTEPPEIFSVKPVLGIKRMIRIEW

IKPELAPVSSDLKYALRFRTVNSTSWMEVNFAKNRKDTNQTYNLMGLQ

AFTEYVVALRCAVKESKFWSDWSQEKMGMTEEEAPCGLELWRVLKPTE

VDGRRPVRLLWKKARGAPVLEKTLGYNIWYFPENNTNLTETVNTTNQQ

LELHLGGESYWVSMISYNSLGKSPVTTLRIPAIQEKSFRCIEVMQACL

AEDQLVVKWQSSALDVNTWMIEWFPDMDSEHPTLSWESVSQATNWTIQ

QDKLKPFWCYNISVYPMLHDKVGEPYSIQAYAKEGIPSKGPETKVENI

GVKTVTITWKEIPKSERKGIICNYTIFYQAEGGKGFSKTVNSSILQYG

LESLKRKTSYTVRVMASTSAGGINGTSINFKTLSFSVFEIILITSLIG

GGLLILIILTVAYGLKKPNKLTHLCWPSVPNPAESSIATWRGDDFKDK

LNLKESDDSVNTEDRILKPCSTPSDKLVIDKSVVNFGNVLQEMFTDEA

RTGQENNLGGEKNEYVTHPFRADCPLGKSFEELPVSPEIPPRKSQYLR

SRMPEGTCLEAEEQLLVSGQSLESLAPDHVREAAAPNPYLKNSVTTRE

FLVSQKLPEHTKGEV

As used herein, the term "subject" is used interchangeably with "patient," and indicates a mammal, in particular a human, equine, bovine, porcine, feline, canine, murine, rat, or non-human primate. In preferred embodiments, the subject is a human. In some embodiments, the subject has been diagnosed of PN for at least 6 months. In particular embodiments, the subject has at least 20 nodules on his/her body with a bilateral distribution. In particular embodiments, the subject has prurigo lesions on upper limbs, with or without lesions on the trunk or lower limbs. In particular embodiments, the subject has pruritus that has been assigned a score of at least 7 on the Numerical Rating Scale (NRS). In particular embodiments, the mean of the worst daily intensity of the NRS score is at least 7 over the previous 3 days. In other particular embodiments, the mean of the worst daily intensity of the NRS score is at least 7 over the previous week.

In some embodiments, the subject does not have atopic dermatitis. In some embodiments, the subject does not have chronic pruritus resulting from a condition other than PN, such as scabies, insect bite, lichen simplex chronicus, psoriasis, acne, folliculitis, habitual picking, lymphomatoid papulosis, chronic actinic dermatitis, dermatitis herpetiformis, sporotrichosis, bullous disease. In some embodiments, the subject does not have neuropathic or psychogenic pruritus, such as notalgia paresthetica, brachioradial pruritus, dilutional parasitosis, pathomimia.

The term "chronic prurigo" or ("CP") is used herein as it is in the art and means a distinct disease defined by the presence of chronic pruritus and multiple localized or generalized pruriginous lesions. Chronic pruritic condition is characterized by excoriated, scaled or crusted plaques and/or papules and/or nodules, often with a whitish or pink center and hyperpigmented border and scars. There are four subtypes of chronic pruritus: nodular type (prurigo nodularits or PN), popular type (papular prurigo), plaque type, and umbilicated type (Kyrle type). CP occurs due to a neuronal sensitization to itch and the development of an itch-scratch cycle. CP can be of dermatological, systemic, neurologic, psychiatric/psychosomatic, multifactorial or undetermined origin. The term CP includes all stages and manefestations of chronic prurigo. The best known subtype of CP is prurigo nodularis (PN). See Pereira et al., *Journal of European Academy of Dermatology and Venereology* (2018) 32:1059-1065.

The term "prurigo nodularis" (or "PN") is used herein as it is in the art and means a skin disease that causes hard, itchy lumps (nodules) to form on the skin. The itching (pruritus) can be intense, causing people to scratch themselves to the point of bleeding or pain. Scratching can cause more skin lesions to appear. The itching is worsened by heat, sweating, or irritation from clothing. In some cases, people with PN have a history of other diseases including eczema (atopic dermatitis), diabetes, lymphoma, HIV infection, severe anemia, or kidney disease. The exact cause of PN is not well-understood. It is thought that nodules are more likely to form when skin has been scratched or irritated in some way. Therefore, the act of a person scratching skin can cause the nodules to form. However, the cause of the skin to originally become intensely itchy is unclear. Many people with PN have a history of eczema (atopic dermatitis), other skin conditions, or allergies. The main symptom of prurigo nodularis (PN) is the formation of hard, very itchy lumps (nodules) on the skin. The nodules can range in size from very small to about half an inch in diameter. The nodules often have a rough, dry top and can range in number from a few to hundreds. Nodules most commonly form on the outer arms, shoulders, and legs. Nodules can also form on the neck and trunk, and they rarely form on the face and palms. They may be lighter or darker in color than the surrounding skin. Scarring may occur after nodules begin to heal. The symptoms of PN can begin at any age but are most common in adults between 20-60 years. People who have PN may become very concerned about the appearance of the nodules, and the intensely itchy skin may interfere with sleep or with everyday activities. This can cause people with PN to develop stress and depression.

The term "pruritus" is used herein as it is in the art and refers to itchy skin and/or an itch sensation. Pruritus may be caused by PN or other diseases or conditions such as dry skin. In some cases, pruritus involves generalized itchy skin over the whole body. In some cases, pruritus is localized to specific regions of the body such as on an arm or leg. Pruritus can be chronic or acute. Symptoms of pruritus include but are not limited to skin excoriations, redness, bumps, spots, blisters, dry skin, cracked skin, and leathery or scaly texture to the skin. In some cases, pruritus does not result in detectable changes to the skin. Behavioral responses to pruritus include but are not limited to skin scratching and/or skin massage. In some cases, skin scratching can result in excoriations that range from mild to severe. In some cases, patients with pruritus abstain from scratching and/or massaging the skin. Traditional treatments for pruritus include but are not limited to skin moisturizers, topical emollients, antihistamines such as diphenhydramine, corticosteroids such as hydrocortisone topical cream, counterirritants such as mint oil, menthol, or camphor, crotamiton, an antipruritic agent often used to treat scabies, local anesthetics such as benzocaine topical cream, and phototherapy. The common type of light used for phototherapy is UVB.

As used herein, the term "antibody" collectively refers to immunoglobulins or immunoglobulin-like molecules including by way of example and without limitation, IgA, IgD, IgE, IgG and IgM, combinations thereof or fragments thereof. Fragments of antibodies including, by way of example and without limitation, Fab fragments and single chain variable fragments (scFv), and similar molecules produced during an immune response in any vertebrate, for example, in mammals such as humans, goats, rabbits and mice, as well as non-mammalian species, such as shark immunoglobulins.

In terms of antibody structure, an immunoglobulin generally has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions, also called the "Fab region," specifically bind the antigen. Light and heavy chain variable regions contain a "framework" region interrupted by three hypervariable regions, also called "complementarity-determining regions" or "CDRs". The extent of the framework region and CDRs has been defined (see, Kabat et al., Sequences of Proteins of Immunological Interest, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopts a (3-sheet conformation and the CDRs form loops which connect, and in some cases form part of, the (3-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds IL-31RA will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs). The base of the antibody plays a role in modulating immune cell activity. This region is called the Fc fragment region (Fc) and is composed of two heavy chains that contribute two or three constant domains depending on the class of the antibody. The Fc region functions to guarantee that each antibody generates an appropriate immune response for a given antigen, by binding to a specific class of proteins found on certain cells, such as B lymphocytes, follicular dendritic cells, natural killer cells, macrophages, neutrophils, etc. and are call "Fc receptors." Because the constant domains of the heavy chains make up the Fc region of an antibody, the classes of heavy chain in antibodies determine their class effects. The heavy chains in antibodies include alpha, gamma, delta, epsilon, and mu, and correlate to the antibody's isotypes IgA, G, D, E, and M, respectively. This infers different isotypes of antibodies have different class effects due to their different Fc regions binding and activating different types of receptors.

There are four subclasses of IgG, which is the most abundant antibody isotype found in human serum. The four subclasses, IgG1, IgG2, IgG3, and IgG4, which are highly conserved. See generally, world wide web: nebi.nlm.nih.gov/pmc/articles/PMC4202688/. The amino acid sequence of the constant regions of these peptides are known in the art, e.g., see Rutishauser, U. et al. (1968) "Amino acid sequence of the Fc region of a human gamma G-immunoglobulin" PNAS 61(4):1414-1421; Shinoda et al. (1981) "Complete amino acid sequence of the Fc region of a human delta chain" PNAS 78(2):785-789; and Robinson et al. (1980) "Complete amino acid sequence of a mouse immunoglobulin alpha chain (MOPC 511)" PNAS 77(8):4909-4913.

Therapeutic Antibodies

"Nemolizumab" is a humanized monoclonal antibody that binds to IL-31RA. Nemolizumab is annotated as follows: immunoglobulin G2-kappa, anti-[*Homo sapiens* IL31RA (interleukin 31 receptor subunit alpha)], humanized monoclonal antibody; gamma2 heavy chain (1-445) [humanized $V_H$ (*Homo sapiens* IGHV1-2*02 (83.70%)-(IGHD)-IGHJ5*01) [8.8.14] (1-121)-*Homo sapiens* IGHG2*01 (CH1 C10>S (135), R12>K (137), E16>G (141), 517>G (142) (122-219), hinge C4>S (223) (220-231), CH2 H30>Q (268) (232-340), CH3 R11>Q (355), Q98>E (419) (341-445)), (122-445)], (224-214')-disulfide with kappa light chain (1'-214') [humanized V-KAPPA (*Homo sapiens* IGKV1-39*01 (82.10%)-IGKJ4*01) [6.3.9] (1'-107')-*Homo sapiens* IGKC*01 (108'-214')]; dimer (227-227":230-230")-bisdisulfide. Nemolizumab has disulfide bridges at the following locations: Intra-H (C23-C104) 22-96 148-204 261-321 367-425 22"-96" 148"-204" 261"-321" 367"-425"'; Intra-L (C23-C104) 23'-88' 134'-194' 23'"-88'" 134'"-194'"; Inter-H-L (h 5-CL 126) 224-214' 224"-214'"; Inter-H-H (h 8, h 11) 227-227" 230-230". Nemolizumab has N-glycosylation sites at the following locations: H CH2 N84.4: 297, 297". Nemolizumab lacks H chain C-terminal glycine and lysine (CHS G1>del, K2>del).

Nemolizumab Heavy Chain Amino Acid Sequence:

(SEQ ID NO: 5)
QVQLVQSGAEVKKPGASVKVSCKASGYTFT*GYIMN*WVRQAPGQGLEW

MGL*INPYNGGTDYNPQFQD*RVTITADKSTSTAYMELSSLRSEDTAVY

YCAR*DGYDDGPYTLET*WGQGTLVTVSSASTKGPSVFPLAPSSKSTSG

GTAALGCLVKDYFPEPVTVSWNSGALTSGVHTFPAVLQSSGLYSLSSV

VTVPSSNFGTQTYTCNVDHKPSNTKVDKTVERKSCVECPPCPAPPVAG

PSVFLFPPKPKDTLMISRTPEVTCVVVDVSQEDPEVQFNWYVDGVEVH

NAKTKPREEQFNSTFRVVSVLTVVHQDWLNGKEYKCKVSNKGLPAPIE

KTISKTKGQPREPQVYTLPPSQEEMTKNQVSLTCLVKGFYPSDIAVEW

ESNGQPENNYKTTPPMLDSDGSFFLYSKLTVDKSRWQEGNVFSCSVMH

EALHNHYTQKSLSLSP

Nemolizumab Light Chain Amino Acid Sequence:

(SEQ ID NO: 6)
DIQMTQSPSSLSASVGDRVTITCQ*ASEDIYSFVA*WYQQKPGKAPKLL

IY*NAQTEAQ*GVPSRFSGSGSGTDFTLTISSLQPEDFATYYC

*QHHYDSPLT*FGGGTKVEIKRTVAAPSVFIFPPSDEQLKSGTASVVCL

LNNFYPREAKVQWKVDNALQSGNSQESVTEQDSKDSTYSLSSTLTLSK

ADYEKHKVYACEVTHQGLSSPVTKSFNRGEC

The variable domains of the heavy and light chain sequences are shown in bold above, and the CDR sequences are underlined/italicized.

Equivalent antibodies to nemolizumab include but are not limited to: (i) antibodies with heavy chains comprising at least 55%, at least 65%, at least 70%, at least 75%, at least 80%, at least 85%, at least 90%, at least 95%, at least 97%, at least 98%, at least 99%, or 100% amino acid sequence identity to nemolizumab's heavy chain sequence, (ii) antibodies with light chains comprising at least 55%, at least 65%, at least 70%, at least 75%, at least 80%, at least 85%, at least 90%, at least 95%, at least 97%, at least 98%, at least 99%, or 100% amino acid sequence identity to nemolizumab's light chain sequence, (iii) antibodies with variable regions comprising at least 55%, at least 65%, at least 70%, at least 75%, at least 80%, at least 85%, at least 90%, at least 95%, at least 97%, at least 98%, at least 99%, or 100% amino acid sequence identity to nemolizumab's variable region sequences, (iv) antibodies with CDRs comprising at least 55%, at least 65%, at least 70%, at least 75%, at least 80%, at least 85%, at least 90%, at least 95%, at least 97%, at least 98%, at least 99%, or 100% amino acid sequence identity to nemolizumab's CDR sequences, (v) antibodies that bind to the same isoform of IL-31RA as nemolizumab (e.g., IL31-RAv3), optionally the same epitope of IL-31RA, (vi) antibodies that block or neutralize IL-31RA, (vii) antibodies that bind to oncostatin M receptor (OSMR), and (viiii) combinations thereof. For example, suitable equivalents include immunoglobulins or immunoglobulin-like molecules with the same or substantially similar heavy and light chain amino acid sequences as nemolizumab. Additional exemplary nemolizumab equivalents are described, for example, in WO 2010/064697.

Equivalents of nemolizumab may be monoclonal or polyclonal antibodies. Such monoclonal antibodies having IL31-RA-binding and/or neutralizing activity can be obtained, for example, by the following procedure: anti-IL31-RA monoclonal antibodies are prepared by using as an antigen IL31-RA or a fragment thereof that is derived from a mammal such as human or mouse by known methods, and then antibodies having IL31-RA-binding and/or neutralizing activity are selected from the thus obtained anti-IL31-RA monoclonal antibodies. Specifically, a desired antigen or cells expressing the desired antigen are used as a sensitizing antigen for immunization according to conventional immunization methods. Anti-IL31-RA monoclonal antibodies can be prepared by fusing the obtained immune cells with known parental cells using conventional cell fusion methods, and screening them for monoclonal antibody-producing cells (hybridomas) by conventional screening methods. Animals to be immunized include, for example, mammals such as mice, rats, rabbits, sheep, monkeys, goats, donkeys, cows, horses, and pigs. The antigen can be prepared using the known IL31-RA gene sequence according to known methods, for example, by methods using baculovirus (for example, WO 98/46777).

Hybridomas can be prepared, for example, according to the method of Milstein et al. (Kohler, G. and Milstein, C., Methods Enzymol. (1981) 73: 3-46). When the immunogenicity of an antigen is low, immunization may be performed after linking the antigen with a macromolecule having immunogenicity, such as albumin. Antigens used to prepare monoclonal antibodies that have a binding and/or neutralizing activity against human IL31-RA are not particularly limited, as long as they enable preparation of antibodies that have a binding and/or neutralizing activity against human IL31-RA. For example, it is known that there are a number of variants of human IL31-RA, and any variant may be used as an immunogen as long as it enables preparation of antibodies that have a binding and/or neutralizing activity against human IL31-RA. Alternatively, under the same condition, a peptide fragment of IL31-RA or a protein in which artificial mutations have been introduced into the natural IL31-RA sequence may be used as an immunogen. Human IL31-RA.3 is one of preferred immunogens in preparing antibodies that have an activity of binding and/or neutralizing IL31-RA in the present disclosure.

The IL31-RA-binding activity of the equivalent antibodies can be determined by methods known to those skilled in the art. Methods for determining the antigen-binding activity of an antibody include, for example, ELISA (enzyme-linked immunosorbent assay), EIA (enzyme immunoassay), RIA (radioimmunoassay), and fluorescent antibody method. For example, when enzyme immunoassay is used, antibody-containing samples, such as purified antibodies and culture supernatants of antibody-producing cells, are added to antigen-coated plates. A secondary antibody labeled with an enzyme, such as alkaline phosphatase, is added and the plates are incubated. After washing, an enzyme substrate, such as p-nitrophenyl phosphate, is added, and the absorbance is measured to evaluate the antigen-binding activity. The binding and/or neutralizing activity of an equivalent antibody against IL31-RA can be measured, for example, by observing the effect of suppressing the growth of the IL-31-dependent cell line. For example, the activity of a purified mouse IL-31 antibody can be assayed by assessing the IL-31-dependent growth of Ba/F3 cells transfected with mouse IL-31 receptor α and mouse OSMR genes.

The inventors have hypothesized that an anti-pruritic drug could have a greater impact on PN in patients that suffer from moderate to severe pruritus.

In some embodiments, pruritus are scored as none, mild, moderate, or severe. "None," "mild," "moderate," and "severe" are terms of art in describing the presence, extent, and/or intensity of excoriations. Those of skill in the art know the metes and bounds of these terms.

In some embodiments, pruritus is characterized according to one or more of the following methods known by those skilled in the art. For example, the intensity can be quickly measured with monodimensional scales that are routinely used in clinical care. See Pereira et al., Allergology International (2017) 66:3-78, incorporated herein by reference. For example, patients can be asked to rate their itch intensity from 0 ("no itch") to 10 ("worst imaginable itch") with the numerical rating scale (NRS). Another monodimensional scale, the visual analogue scale (VAS), provides patients with the opportunity to indicate the intensity of their itch by marking on a 10 cm long, ruler-shaped scale. Both endpoints are marked with a number corresponding to the intensity, with 0 representing "no itch" and 10 the "worst imaginable itch." Scores below 3.0 VAS/NRS points are generally associated with mild itch, whereas scores higher than 6.9 illustrate severe itch. Scores above 9.0 represent a very severe itch. The verbal rating scale (VRS) is a further monodimensional scale that allows patients to describe their itch intensity by means of gradually rising adjectives (0—no itch, 4—worst imaginable itch). The NRS, VAS and VRS have been validated in large-scale studies consisting of chronic pruritus patients with pruritic dermatoses or pruritus of various origins. These instruments have high reproducibility and there was a high correlation between scales 6, 7, 8. Chronic pruritus can greatly reduce patient quality of life. For this reason, Dermatology Life Quality Index (DLQI) is widely used and has been validated. DLQI scores range from 0 to 30, with higher scores indicating a lower quality of life. Investigators' Global Assessment (IGA) scores range from 0 (clear) to 5 (very severe disease) and are presented as a percentage of patients in the indicated population. In the present study, IGA scores range from 0 to 4.

Pharmaceutical Compositions

Provided herein are pharmaceutical compositions for use in the treatment of skin lesions and pruritus in a subject having chronic prurigo (CP), the composition comprising, consisting of, or consisting essentially of nemolizumab or an equivalent thereof. Moreover, the present disclosure provides therapeutic agents for CP which comprise nemolizumab or an equivalent thereof as an active ingredient.

In some embodiments, the subject has prurigo nodularis (PN). In some embodiments, the subject has been diagnosed of PN for at least about 6 months. In particular embodiments, the subject has at least about 20 nodules on his/her body with a bilateral distribution. In particular embodiments, the subject has prurigo lesions on upper limbs, with or without lesions on the trunk or lower limbs. In particular embodiments, the pruritus has been assigned a score of at least 7 on the Numerical Rating Scale (NRS). In particular embodiments, the mean of the worst daily intensity of the NRS score is at least 7 over the previous 3 days. In other particular embodiments, the mean of the worst daily intensity of the NRS score is at least 7 over the previous week.

In some embodiments, the subject does not have atopic dermatitis. In some embodiments, the subject does not have chronic pruritus resulting from a condition other than PN, such as scabies, insect bite, lichen simplex chronicus, psoriasis, acne, folliculitis, habitual picking, lymphomatoid papulosis, chronic actinic dermatitis, dermatitis herpetiformis, sporotrichosis, bullous disease. In some embodiments, the subject does not have neuropathic or psychogenic pruritus, such as notalgia paresthetica, brachioradial pruritus, dilutional parasitosis, pathomimia.

The phrase "comprise(s) nemolizumab or an equivalent thereof as an active ingredient" means comprising nemolizumab or an equivalent thereof as at least one of the active ingredients, and does not limit the proportion of the antibody. In addition, the therapeutic agents for PN in the present disclosure may also comprise, in combination with nemolizumab or an equivalent thereof, other ingredients that enhance the treatment of PN. For example, the composition may comprise one or more topical corticosteroid creams or injections, ointments with menthol or phenol to cool and soothe itchy skin, capsaicin cream, oral corticoseroids, selective serotonin reuptake inhibitors (SSRIs), and oral antihistamines.

Pharmaceutical compositions of nemolizumab or an equivalent thereof of the present disclosure can be prepared as formulations according to standard methods (see, for example, Remington's Pharmaceutical Science, Mark Publishing Company, Easton, USA). In some embodiments, the pharmaceutical compositions comprise a carrier and/or additive. In some embodiments, the carrier is a pharmaceutically acceptable carrier. For example, in some embodiments, the pharmaceutical composition comprises one or more surfactants (for example, PEG and Tween), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, corrigents, light anhydrous silicic acid, lactose, crystalline cellulose, mannitol, starch, carmelose calcium, carmelose sodium, hydroxypropylcellulose, hydroxypropylmethylcellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, and inorganic salt. In some embodiments, the pharmaceutical composition comprises one or more other low-molecular-weight polypeptides, proteins such as serum albumin, gelatin, and immunoglobulin, and amino acids such as glycine, glutamine, asparagine, arginine, and lysine.

When nemolizumab or an equivalent thereof is prepared as an aqueous solution for injection, nemolizumab or an equivalent thereof may be dissolved in an isotonic solution containing, for example, physiological saline, dextrose, or other adjuvants. The adjuvants may include, for example, D-sorbitol, D-mannose, D-mannitol, and sodium chloride. In addition, appropriate solubilizing agents, for example, alcohols (for example, ethanol), polyalcohols (for example, propylene glycols and PEGs), and non-ionic detergents (polysorbate 80 and HCO-50) may be used concomitantly.

If necessary, nemolizumab or an equivalent thereof may be encapsulated in microcapsules (microcapsules made of hydroxymethylcellulose, gelatin, polymethylmethacrylate, and the like), and made into components of colloidal drug delivery systems (liposomes, albumin microspheres, microemulsions, nano-particles, and nano-capsules) (for example, see "Remington's Pharmaceutical Science 16th edition" &, Oslo Ed. (1980)). Moreover, methods for making sustained-release drugs are known, and these can be applied for nemolizumab or an equivalent thereof (Langer et al., J. Biomed. Mater. Res. (1981) 15, 167-277; Langer, Chem. Tech. (1982) 12, 98-105; U.S. Pat. No. 3,773,919; European Patent Application (EP) No. 58,481; Sidman et al., Biopolymers (1983) 22, 547-56; EP 133,988).

The pharmaceutical compositions of the present disclosure can be administered either orally or parenterally, but are preferably administered parenterally. Specifically, the pharmaceutical compositions are administered to patients by injection or percutaneous administration. Injections include, for example, intravenous injections, intramuscular injections, and subcutaneous injections, for systemic or local administration. The pharmaceutical compositions may be given to sites where inflammation is to be suppressed, or areas surrounding the sites by local infusion or intramuscular injection. In some embodiments, the pharmaceutical compositions are administered at the site of one or more skin excoriations, or proximal to the site of one or more skin excoriations.

The administration methods can be properly selected according to the patient's age and condition. The single-administration dose can be selected, for example, from within the range of 0.0001 to 100 mg of the active ingredient per kg body weight. Alternatively, for example, when the agents are administered to human patients, the dose of the active ingredient can be selected from within the range of 0.001 to 1,000 mg/kg body weight. In some embodiments, the composition is formulated to administer a dose containing, for example, about 0.01 to 50 mg/kg, about 0.01 mg/kg to about 0.1 mg/kg, about 0.05 mg/kg to 0.15 mg/kg, about 0.1 mg/kg to about 0.6 mg/kg, about 0.1 mg/kg to about 1 mg/kg, about 0.25 mg/kg to about 0.75 mg/kg, about 0.4 mg/kg to about 0.8 mg/kg, about 0.4 mg/kg to about 1.8 mg/kg, about 0.5 to about 2.5 mg/kg, about 0.8 mg/kg to about 2.2 mg/kg, about 1 mg/kg to about 2.5 mg/kg, about 1 mg/kg to about 3.5 mg/kg, about 1 mg/kg to about 5 mg/kg, about 2 mg/kg to about 4 mg/kg, about 2.5 mg/kg to about 10 mg/kg, about 5 mg/kg to about 10 mg/kg, about 10 mg/kg to about 20 mg/kg, about 10 mg/kg to about 40 mg/kg, about 20 mg/kg to about 50 mg/kg, about 25 mg/kg to about 75 mg/kg, about 50 mg/kg to about 100 mg/kg, or about 100 mg/kg to about 500 mg/kg, or about 100 mg/kg to about 1000 mg/kg body weight of nemolizumab or an equivalent thereof. In preferred embodiments, the dose ranges from about 0.01 mg/kg to about 0.1 mg/kg, about 0.1 mg/kg to about 0.5 mg/kg, about 0.5 mg/kg to about 1.5 mg/kg, about 1.5 mg/kg to about 2.5 mg/kg, or about 2.5 mg/kg to about 10 mg/kg. In some embodiments, the dose is about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3 mg/kg, about 3.5 mg/kg, about 4 mg/kg, about 4.5 mg/kg, about 5 mg/kg, about 6 mg/kg, about 7 mg/kg, about 8 mg/kg, about 9 mg/kg, about 10 mg/kg, about 15 mg/kg, about 25 mg/kg, about 50 mg/kg, about 75 mg/kg, about 100 mg/kg, about 500 mg/kg, or about 1,000 mg/kg. In particular embodiments, the effective amount of nemolizumab or the equivalent thereof is about 0.1 mg/kg, about 0.5 mg/kg, about 1 mg/kg, about 1.5 mg/kg, about 2 mg/kg, or about 2.5 mg/kg. In a preferred embodiment, the dose is about 0.5 mg/kg.

Methods of Treatment

In accordance with some embodiments, there are provided methods of treating pruritus in a subject having prurigo nodularis (PN), the method comprising, consisting of, or consisting essentially of administering an effective amount of nemolizumab or an equivalent thereof to the subject.

In some embodiments, the pruritus is moderate to severe. In some embodiments of the methods, the subject has been diagnosed of PN for at least 6 months. In particular embodiments of the methods, the subject has at least 20 nodules on his/her body with a bilateral distribution. In particular embodiments of the methods, the subject has prurigo lesions on upper limbs, with or without lesions on the trunk or lower limbs. In particular embodiments of the methods, the pruritus has been assigned a score of at least 7 on the Numerical Rating Scale (NRS). In particular embodiments of the methods, the mean of the worst daily intensity of the NRS score is at least 7 over the previous 3 days. In other particular embodiments of the methods, the mean of the worst daily intensity of the NRS score is at least 7 over the previous week.

In some embodiments of the methods, the subject does not have atopic dermatitis. In some embodiments of the methods, the subject does not have chronic pruritus resulting from a condition other than PN, such as scabies, insect bite, lichen simplex chronicus, psoriasis, acne, folliculitis, habitual picking, lymphomatoid papulosis, chronic actinic dermatitis, dermatitis herpetiformis, sporotrichosis, bullous disease. In some embodiments of the methods, the subject does not have neuropathic or psychogenic pruritus, such as notalgia paresthetica, brachioradial pruritus, dilutional parasitosis, pathomimia.

An "effective amount" is an amount sufficient to effect beneficial or desired results such as alleviating at least one or more symptom of PN and/or pruritus. An effective amount as used herein would also include an amount sufficient to delay the development of AD and/or pruritus, alter the course of an PN and/or pruritus symptom (for example sleep efficiency), or reverse a symptom of PN and/or pruritus. Thus, it is not possible to specify the exact "effective amount." However, for any given case, an appropriate "effective amount" can be determined by one of ordinary skill in the art using only routine experimentation.

An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present disclosure for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. The dosage can be determined by a physician and adjusted, as necessary, to suit observed effects of the treatment. Typically, dosage-effect relationships from in vitro and/or in vivo tests initially can provide useful guidance on the proper doses for patient administration. In general, one will desire to administer an amount of the compound that is effective to achieve a serum level commensurate with the concentrations found to be effective in vitro. Determination of these parameters is well within the skill of the art. These considerations, as well as effective formulations and administration procedures are well known in the art and are described in standard textbooks.

Dosage regimens for treating CP and PN may comprise flat dosing (i.e., administering the same dose repeatedly at pre-determined intervals) or comprise a loading dose (i.e., administrating an initial dose that is higher or different than subsequent, serial doses). For the purposes of either type of dosing regimen an effective dose may be administered topically, parenterally, subcutaneously, subdermally, intradermally, or intramuscularly.

In some embodiments, a loading dose and the subsequent serial doses may be administered via the same route (e.g., subcutaneously), while in some embodiments, a loading dose and the subsequent serial doses may be administered via different routes (e.g., parenterally and subcutaneously, respectively). In some embodiments, the loading dose may be about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, or higher. In some embodiments, the loading dose may be 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, or higher. In some embodiments, the loading dose may be about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3 mg/kg, about 3.5 mg/kg, about 4 mg/kg, about 4.5 mg/kg, about 5 mg/kg, about 6 mg/kg, about 7 mg/kg, about 8 mg/kg, about 9 mg/kg, about 10 mg/kg, about 15 mg/kg, about 25 mg/kg, about 50 mg/kg, about 75 mg/kg, about 100 mg/kg, about 500 mg/kg, or about 1,000 mg/kg. In some embodiments, the loading dose may be 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.5 mg/kg, 4 mg/kg, 4.5 mg/kg, 5 mg/kg, 6 mg/kg, 7 mg/kg, 8 mg/kg, 9 mg/kg, 10 mg/kg, 15 mg/kg, 25 mg/kg, 50 mg/kg, 75 mg/kg, 100 mg/kg, 500 mg/kg, or 1,000 mg/kg. In some embodiments, the loading dose is administered as a single injection. In some embodiments, the loading dose is administered as multiple injections, which may be administered at the same time or spaced apart at defined intervals.

The subsequent serial doses of a loading dose regimen are generally lower than the loading dose. For examples, in some embodiments, the dosing regimen may comprise a loading dose of 60 mg and a serial dose of 30 mg, which may be administered a defined intervals of, for example, every 4 weeks. In some embodiments, the serial dose of a dosing regimen may be about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, or higher. In some embodiments, the serial dose may be 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, or higher. In some embodiments, the serial dose may be about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3 mg/kg, about 3.5 mg/kg, about 4 mg/kg, about 4.5 mg/kg, about 5 mg/kg, about 6 mg/kg, about 7 mg/kg, about 8 mg/kg, about 9 mg/kg, about 10 mg/kg, about 15 mg/kg, about 25 mg/kg, about 50 mg/kg, about 75 mg/kg, about 100 mg/kg, about 500 mg/kg, or about 1,000 mg/kg. In some embodiments, the serial dose may be 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.5 mg/kg, 4 mg/kg, 4.5 mg/kg, 5 mg/kg, 6 mg/kg, 7 mg/kg, 8 mg/kg, 9 mg/kg, 10 mg/kg, 15 mg/kg, 25 mg/kg, 50 mg/kg, 75 mg/kg, 100 mg/kg, 500 mg/kg, or 1,000 mg/kg.

For the purposes of a loading dose regimen, the first serial dose may be administered 1 day, 2 days, 3 days, 4 days, 5 days, 6 days, 7 days, 8 days, 9 days, 10 days, 11 days, 12 days, 13 days, 1 week, 2 weeks, 3 weeks, 4 weeks, 5 weeks, 6 weeks, 7 weeks, 8 weeks, 9 weeks, or 10 weeks after the initial loading dose. In some embodiments, the first serial dose is administered 4 weeks after the initial loading dose. In some embodiments, the subsequent serial doses are administered once every 1 day, 2 days, 3 days, 4 days, 5 days, 6 days, 7 days, 8 days, 9 days, 10 days, 11 days, 12 days, 13 days, 1 week, 2 weeks, 3 weeks, 4 weeks, 5 weeks, 6 weeks, 7 weeks, 8 weeks, 9 weeks, or 10 weeks. In some embodiments, the serial doses are spaced 4 weeks apart (i.e., nemolizumab or an equivalent thereof is administered once every 4 weeks).

In some embodiments, the dose of nemolizumab or an equivalent thereof administered to the subject is within the range of 0.001 to 1,000 mg/kg body weight of the subject. In some embodiments, the dose ranges from about 0.01 to 50 mg/kg, about 0.01 mg/kg to about 0.1 mg/kg, about 0.05 mg/kg to 0.15 mg/kg, about 0.1 mg/kg to about 0.6 mg/kg, about 0.1 mg/kg to about 1 mg/kg, about 0.25 mg/kg to about 0.75 mg/kg, about 0.4 mg/kg to about 0.8 mg/kg, about 0.4 mg/kg to about 1.8 mg/kg, about 0.5 to about 2.5 mg/kg, about 0.8 mg/kg to about 2.2 mg/kg, about 1 mg/kg to about 2.5 mg/kg, about 1 mg/kg to about 3.5 mg/kg, about 1 mg/kg to about 5 mg/kg, about 2 mg/kg to about 4 mg/kg, about 2.5 mg/kg to about 10 mg/kg, about 5 mg/kg to about 10 mg/kg, about 10 mg/kg to about 20 mg/kg, about 10 mg/kg to about 40 mg/kg, about 20 mg/kg to about 50 mg/kg, about 25 mg/kg to about 75 mg/kg, about 50 mg/kg to about 100 mg/kg, about 100 mg/kg to about 500 mg/kg, or about 100 mg/kg to about 1000 mg/kg body weight of nemolizumab or an equivalent thereof. In preferred embodiments, the dose ranges from about 0.01 mg/kg to about 0.1 mg/kg, about 0.1 mg/kg to about 0.5 mg/kg, about 0.5 mg/kg to about 1.5 mg/kg, about 1.5 mg/kg to about 2.5 mg/kg, or about 2.5 mg/kg to about 10 mg/kg. In some embodiments, the dose is about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3 mg/kg, about 3.5 mg/kg, about 4 mg/kg, about 4.5 mg/kg, about 5 mg/kg, about 6 mg/kg, about 7 mg/kg, about 8 mg/kg, about 9 mg/kg, about 10 mg/kg, about 15 mg/kg, about 25 mg/kg, about 50 mg/kg, about 75 mg/kg, about 100 mg/kg, about 500 mg/kg, or about 1,000 mg/kg. In particular embodiments, the effective amount of nemolizumab or the equivalent thereof is about 0.1 mg/kg, about 0.5 mg/kg, about 1 mg/kg, about 1.5 mg/kg, about 2 mg/kg, or about 2.5 mg/kg. In a preferred embodiment, the dose is about 0.5 mg/kg.

In some embodiments, the dose of nemolizumab or an equivalent thereof administered to the subject is within the range of 1 to 100 mg, 25 to 75 mg, 30 to 60 mg, 40 to 80 mg, 20 to 80 mg, 1 to 25 mg, 1 to 50 mg, 10 to 90 mg, 15 to 85 mg, or ranges there between. In some embodiments, the dose may be about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, or higher. In some embodiments, the dose may be 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, or higher.

In particular embodiments, a loading dose of about 60 mg of nemolizumab or an equivalent thereof may be administered to a subject in need thereof, followed by subsequent serial doses of nemolizumab of an equivalent thereof at about 30 mg once every 4 weeks.

In some embodiments of the methods, the nemolizumab or the equivalent thereof is administered by a topical or parenteral route. In some embodiments of the methods, the nemolizumab or the equivalent thereof is administered subcutaneously. In some embodiments, the dose is administered subcutaneously at or proximal to a site of one or more nodules.

In some embodiments, nemolizumab or the equivalent thereof is administered daily, every other day, twice per week, three times per week, four times per week, five times per week, six times per week, once per week, once every two weeks, once every three weeks, once every four weeks, once every five weeks, once every six weeks, once every seven weeks, once every eight weeks, once every nine weeks, once every 10 weeks, once every 11 weeks, once every 12 weeks, twice per year, once per year, and/or as needed based on the appearance of symptoms of atopic dermatitis or pruritus (e.g., CP or PN). In preferred embodiments, nemolizumab or the equivalent thereof is administered every four weeks or every eight weeks.

In some embodiments, the duration of treatment is about one day, about one week, about two weeks, about three weeks, about four weeks, about five weeks, about six weeks, about seven weeks, about eight weeks, about nine weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 24 weeks, about 30 weeks, about 36 weeks, about 40 weeks, about 48 weeks, about 50 weeks, about one year, about two years, about three years, about four years, about five years, or as needed based on the appearance of symptoms of atopic dermatitis or pruritus (e.g., CP or PN). In preferred embodiments, duration of treatment is about 12 weeks to about 24 weeks, about 12 to about 36 weeks, about 12 to about 48 weeks, or about 24 to about 36 weeks.

In accordance with some embodiments, there are provided uses of nemolizumab or an equivalent thereof in the manufacture of a medicament for the treatment of pruritus s in a subject having prurigo nodularis (PN).

In some embodiments of the uses, the pruritus is moderate to severe. In some embodiments of the uses, the subject has been diagnosed of PN for at least 6 months. In particular embodiments of the uses, the subject has at least 20 nodules on his/her body with a bilateral distribution. In particular embodiments of the uses, the subject has prurigo lesions on upper limbs, with or without lesions on the trunk or lower limbs. In particular embodiments of the methods, the pruritus has been assigned a score of at least 7 on the Numerical Rating Scale (NRS). In particular embodiments of the uses, the mean of the worst daily intensity of the NRS score is at least 7 over the previous 3 days. In other particular embodiments of the uses, the mean of the worst daily intensity of the NRS score is at least 7 over the previous week.

In some embodiments of the uses, the subject does not have atopic dermatitis. In some embodiments of the uses, the subject does not have chronic pruritus resulting from a condition other than PN, such as scabies, insect bite, lichen simplex chronicus, psoriasis, acne, folliculitis, habitual picking, lymphomatoid papulosis, chronic actinic dermatitis, dermatitis herpetiformis, sporotrichosis, bullous disease. In some embodiments of the uses, the subject does not have neuropathic or psychogenic pruritus, such as notalgia paresthetica, brachioradial pruritus, dilutional parasitosis, pathomimia.

EXAMPLES

Example 1 Determine Efficacy of Nemolizumab in the Treatment of Pruritus of PN Patients A multi-center (20 sites in EU & US), randomized, double-blinded, placebo-controlled, parallel group study was conducted comprising approximately 70 randomized patients in 2 arms (35 per arm) stratified on background of atopy. Enrolled patients received subcutaneous nemolizumab or placebo at a dose of 0.5 mg/kg every 4 weeks. The patients were selected based on the following criteria.

Inclusion Criteria:
1. Male or female of at least 18 years at screening.
2. Clinical diagnosis of PN for at least 6 months with: (a) Prurigo lesions on upper limbs with or without lesions on the trunk or lower limbs, and (b) at least 20 nodules on the entire body with a bilateral distribution
3. Severe pruritus on a Numerical Rating Scale (NRS). NRS is determined both by screening visit and baseline visit. Screening visit: Mean of the worst daily intensity of the NRS score is ≥7 over the previous 3 days. Baseline visit: Mean of the worst daily intensity of the NRS score is ≥7 over the previous week.
4. Female subjects must fulfill one of the criteria: (a) Female subjects of non-childbearing potential (postmenopausal, i.e. absence of menstrual bleeding for 1 year prior to screening, without any other medical reason, hysterectomy or bilateral oophorectomy); (b) Female subjects of childbearing potential who agree to a true abstinence (when in line with the preferred and usual lifestyle of the subject), or to use an effective method of contraception throughout the clinical trial and for 120 days after the last study drug administration.

Patients with the following conditions are excluded.

Exclusion Criteria:
1. Chronic pruritus resulting from another condition than PN such as scabies, insect bite, lichen simplex chronicus, psoriasis, acne, folliculitis, habitual picking, lymphomatoid papulosis, chronic actinic dermatitis, dermatitis herpetiformis, sporotrichosis, bullous disease.
2. Unilateral lesions of prurigo (e.g only one arm affected)
.
3. Cutaneous bacterial or viral infection within 1 week before the baseline visit.
4. Infection requiring treatment with oral or parenteral antibiotics, antivirals, antiparasitics or antifungals within 1 week before the screening visit, or during the screening period, unless completely resolved at the screening/baseline visits respectively.
5. Any uncontrolled or serious disease, or any medical or surgical condition, that may either interfere with the interpretation of the clinical trial results and/or put the subject at significant risk according to Investigator's judgment (e.g. solid cancer, AIDS, serious or uncontrolled cardiac disease) at Screening or Baseline.

Any active dermatoses that would need immediate therapy.
7. Active atopic dermatitis or known with recurrent flares of atopic dermatitis
8. Neuropathic and psychogenic pruritus (notalgia paresthetica, brachioradial pruritus, dilutional parasitosis, pathomimia).
9. Positive serology results hepatitis B surface antigen (HBsAg) or hepatitis B core antibody (HBcAb), hepatitis C antibody or Human Immunodeficiency virus (HIV) antibody) at the screening visit.
10. Abnormal lab criteria listed below, at the screening visit: Elevated ALT/AST ≥3 ULN, Elevated CPK >1.5 ULN, Neutrophil count <1.5×10$^3$/μl, Creatinine clearance <60 ml/min/1.73 m$^2$;
11. Medical history of asthma that fulfill any or more of the conditions: (i) had an asthma exacerbation requiring hospitalization in the last 12 months before screening visit; (ii) Whose asthma has not been well-controlled (i.e. symptoms >2 days per week, nighttime awakenings >1-3 times per week, or some interference with normal activities) during the last 3 months before the screening visit; PEF <80% of the predicted value at screening or baseline visit.

12. Latent or active TB, as determined by a positive Quantiferon-based TB test result at screening visit.
13. Having received any of forbidden treatments within the specified time frame prior to the baseline visit:

TABLE 1

Forbidden Therapies

| Topical treatments | Wash-out periods |
|---|---|
| Calcineurin inhibitors (tacrolimus, pimecrolimus), TCS, vitamin D analogs, PDE-4 inhibitors | 2 weeks |
| Any topical treatment other than moisturizer (e.g capsaicin, cryotherapy) | 2 weeks |
| Emollients or moisturizer with menthol, capsaicine, polidocanol or other having "anti-itch" claim | 1 week |
| Systemic treatments | Wash-out periods |
| Corticosteroids oral, injectable | 4 weeks |
| immunosuppressive or immunomodulatory drugs (e.g, azathioprine, methotrexate, thalidomide, cyclosporine | 8 weeks or 5 half-lives (whichever is longer) |
| Antihistamines | 1 week |
| Phototherapy | 4 weeks |
| Roxithromycin, erythromycin | 1 week |
| Opiods (naltrexone, naloxone, nalbuphine etc), NK1 receptor antagonists (aprepitant), antiepileptics (gabapentin, pregabalin) | 4 weeks or 5 half-lives (whichever is longer) |
| Biologies, Retinoids | 8 weeks or 5 half-lives (whichever is longer) |
| Live vaccine | 4 weeks |
| Drugs with sedative effect such as benzodiazepines, imidazopyridines, hydroxizine barbiturates, or sedative anti-depressants such as amitryptiline, paroxetine, except if these treatments were taken at a stable dose for at least 3 months before screening | 3 months |

If deemed to be medically necessary by the Investigator, rescue treatments for pruritus could be associated to the study drug from Day 29. All efficacy and safety assessments should be completed before starting the rescue treatments.

TABLE 2

Rescue Therapies

| Rescue therapies | Action to be taken |
|---|---|
| Antihistamines, association of antihistamines and TCS of mid-potency | Continue the study drug |
| cyclosporine, thalidomide, gabapentin, phototherapy, etc . . . | Discontinue the study drug |

Endpoints:
The primary endpoint of the study was a percent reduction from baseline (BL) in pruritus NRS at week 4.
The secondary endpoints of the study was a reduction at every visit up to 18 weeks, characterized by NRS, VRS, or DPS. Safety evaluations were also conducted at the secondary endpoint. Prurigo remission was characterized by prurigo activity score (PAS) and IGA. Pharmacokinetic (PK) profile of PN patients was measured. Pharmacodynamic (PD) profile of PN patients was measured in patients' blood, biopsies, and D-squames samples. Quality of life of PN patients was measured by DLQI. Actigraphy was applied to assess sleep improvement and scratching (by Actiwatch). Photographs of PN patients were taken by fotofinder in selected centers.
The results of the clinical study are presented in the tables below.

TABLE 3

Demographics and baseline characteristics

| | Placebo (N = 36) | Nemolizumab 0.5 mg/kg (N = 34) | Total (N = 70) |
|---|---|---|---|
| Gender | | | |
| Male | 14 (38.9%) | 15 (44.1%) | 29 (41.4%) |
| Female | 22 (61.1%) | 19 (55.9%) | 41 (58.6%) |
| Race | | | |
| White | 35 (97.2%) | 33 (97.1%) | 68 (97.1%) |
| Black/African American | 1 (2.8%) | 1 (2.9%) | 2 (2.9%) |
| Asian | 0 | 0 | 0 |
| Other | 0 | 0 | 0 |
| Age (years) | | | |
| Mean (SD) | 52.4 (17.47) | 59.7 (13.16) | 56.0 (15.85) |
| Range | 20-77 | 26-85 | 20-85 |
| Weight | 36 | 34 | 70 |
| Mean (SD) (kg) | 80.30 (20.716) | 81.61 (21.766) | 80.94 (21.088) |

Note:
Percentages are based on the number of subjects having a non-missing value in the respective treatment arm.

As shown in Table 3, the placebo group and the nemolizumab treated group in the study presented comparable composition in gender, race, age, and weight.

TABLE 4

Baseline clinical disease characteristics

| | Placebo (N = 36) | Nemolizumab 0.5 mg/kg (N = 34) | Total (N = 70) |
|---|---|---|---|
| Mean Prurigo baseline assessment (PAS) (SD) | 22.4 (17.50) | 17.1 (13.39) | 19.8 (15.76) |
| Background of atopy | | | 1 |
| Presence | 6 (16.7%) | 5 (14.7%) | 1 (15.7%) |
| Absence | 30 (83.3%) | 29 (85.3%) | 59 (84.3%) |
| Number of nodules on the entire body n (%) | | | |
| 20-100 | 21 (58.3) | 21 (61.8) | 42 (60.0) |
| >100 | 15 (41.7) | 13 (38.2) | 28 (40.0) |
| Weekly peak pruritus NRS | | | |
| Mean ± SD | 8.4 (1.18) | 8.4 (1.19) | 8.4 (1.17) |
| Range | (7-9) | (8-9) | (8-9) |
| Weekly avg pruritus NRS | 34 | 33 | 67 |
| Mean (SD) | 7.9 (1.28) | 7.8 (1.66) | 7.9 (1.47) |
| Investigator Global Assessment (IGA) n (%) | | | |
| Moderate | 22 (61.1) | 16 (47.1) | 38 (54.3) |
| Severe | 14 (38.9) | 18 (52.9) | 32 (45.7) |
| DLQI baseline score (range 0-30) | | | |
| Mean ± SD | 15.8 ± 6.0 | 16.9 ± 7.5 | |

As shown in Table 4, the placebo group and the nemolizumab treated group in the study presented comparable baseline level of pruritus, measured by number of nodules on the entire body, weekly peak pruritus numerical rating scale (NRS) score, weekly average pruritus NRS score, and Investigator's global assessment (IGA) score.

TABLE 5

Incidence of Rescue Medication

|  | Placebo (N = 36) | Nemolizumab 0.5 mg/kg (N = 34) | Total (N = 70) |
|---|---|---|---|
| Subject with ≥1 rescue medications during treatment period | 4 (11.1%) | 2 (5.9%) | 6 (8.6%) |
| Type of rescue during treatment period: |  |  |  |
| Topical rescue medication (n) | 4 (11.1%) | 0 | 4 (5.7%) |
| Systemic rescue medication (n) | 3 (8.3%) | 2 (5.9%) | 5 (7.1%) |

As shown in Table 5, the placebo group has more incidence of topical rescue medication and systemic rescue medication.

Figure 2:
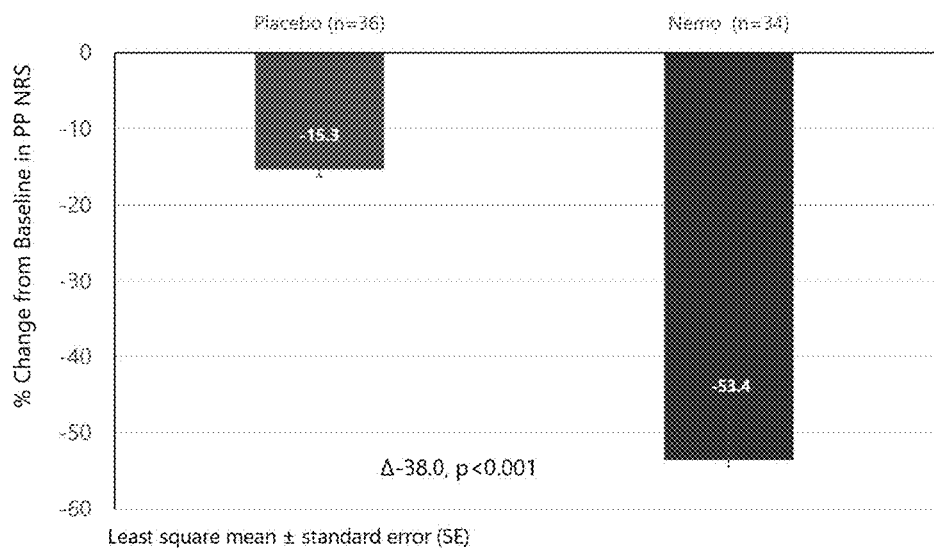
FIG. 2 illustrates percentage change from baseline in weekly average peak pruritus numerical rating score (NRS) at Week 4.
Figure 3:
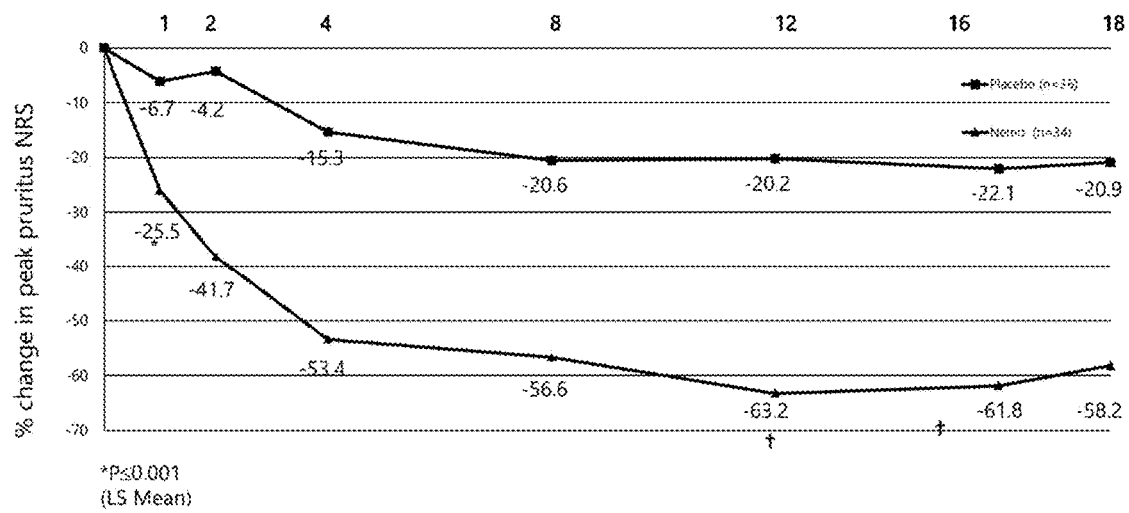
FIG. 3 illustrates percentage change from baseline in weekly average peak pruritus NRS over 18 weeks.
Figure 4:
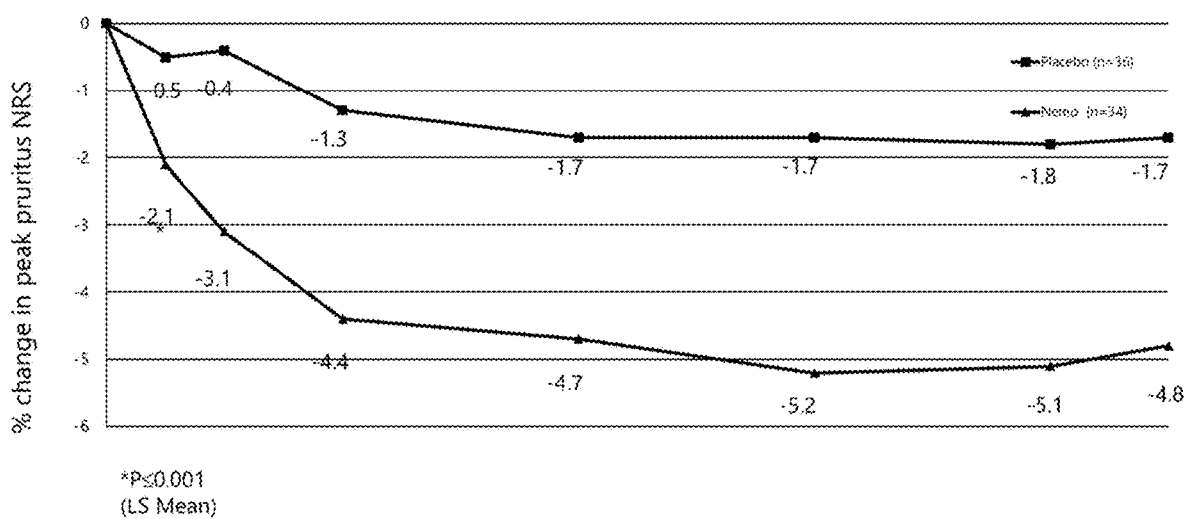
FIG. 4 illustrates absolute change from baseline in weekly average peak pruritus NRS over 18 weeks.

The efficacy results are shown by FIGS. 2-15. In particular, at primary endpoint, the nemolizumab treatment significantly reduced pruritus at week 4, as illustrated by the percentage change from baseline in weekly average peak pruritus NRS (FIG. 2). Thus, nemolizumab treatment at the dosage of 0.5 mg/kg is superior to placebo (−38%, 95% CI=[−51%, −25%] and statistically significant (p<0.001) at Week 4.

Figure 5:
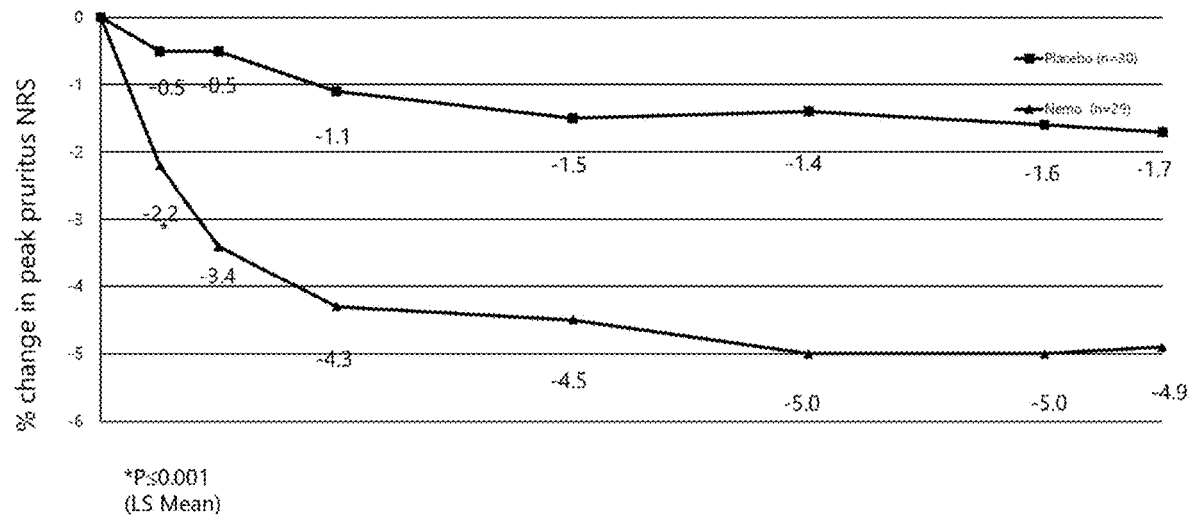
FIG. 5 illustrates absolute change from baseline in weekly average peak pruritus NRS over 18 weeks in patients with no atopy.
Figure 6:
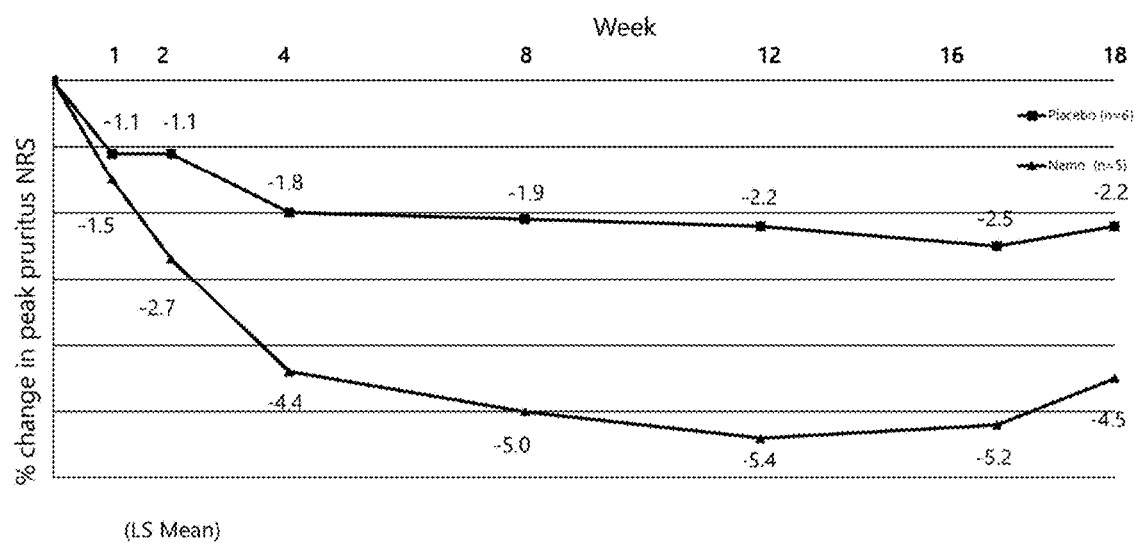
FIG. 6 illustrates absolute change from baseline in weekly average peak pruritus NRS over 18 weeks in patients with atopy.

At secondary endpoints, the nemolizumab treatment group consistently shows more reduced pruritus throughout the 18 weeks study, as evidenced by both the percentage change (FIG. 3) and the absolute change (FIG. 4) in peak pruritus NRS, and the results are statistically significant (p<0.001). The same results were also observed both in patients without or with atopic dermatitis (FIGS. 5 and 6).

Figure 7:
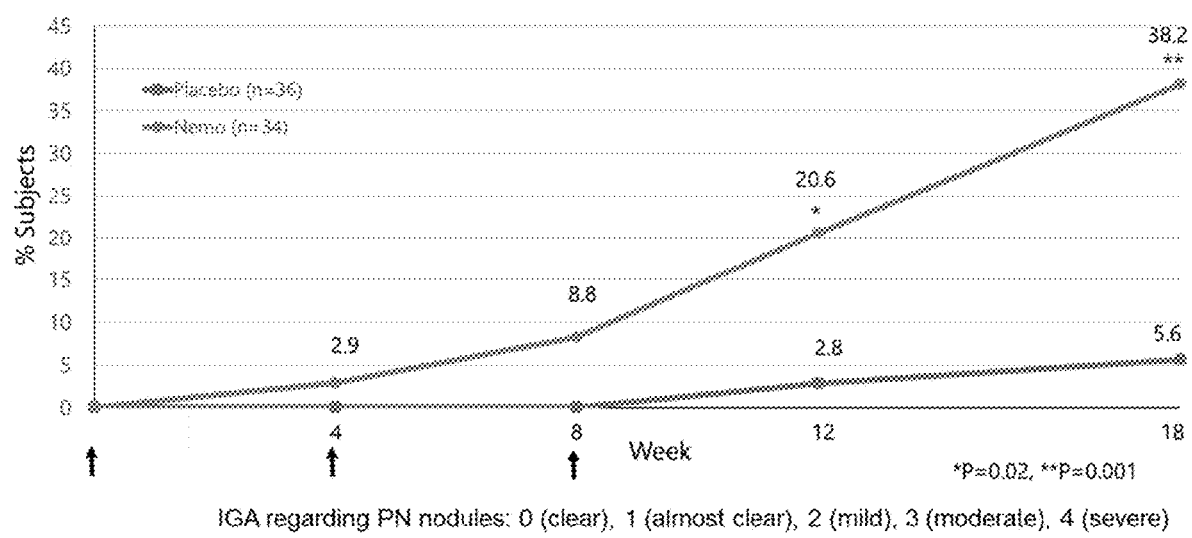
FIG. 7 illustrates proportion of subjects achieving Investigators' Global Assessment (IGA) success (0/1). Investigators' Global Assessment (IGA) scores range from 0 (clear) to 4 (severe disease) and are presented as a percentage of patients in the indicated population.
Figure 8:
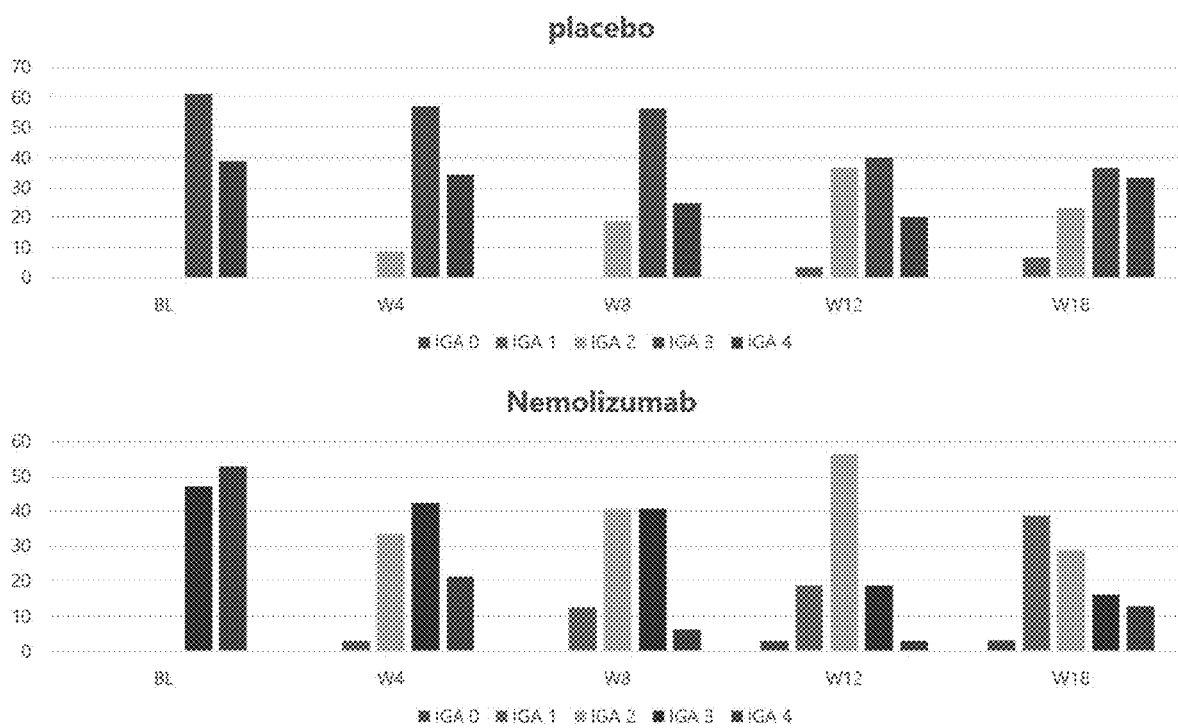
FIG. 8 illustrates IGA distribution in patients over 18 weeks treatment.

Investigators' Global Assessment (IGA) scores range from 0 (clear) to 4 (severe disease) and are presented as a percentage of patients in the indicated population. A much higher percentage of patients treated with nemolizumab compared to the placebo group achieved IGA success (IGA 0/1) (FIG. 7). In addition, IGA distribution shows that the nemolizumab treatment group has consistently higher percentage of patients with lower IGA than the placebo group (FIG. 8). The findings are statistically significant (p<0.05) at Week 12 and Week 18.

Figure 9:
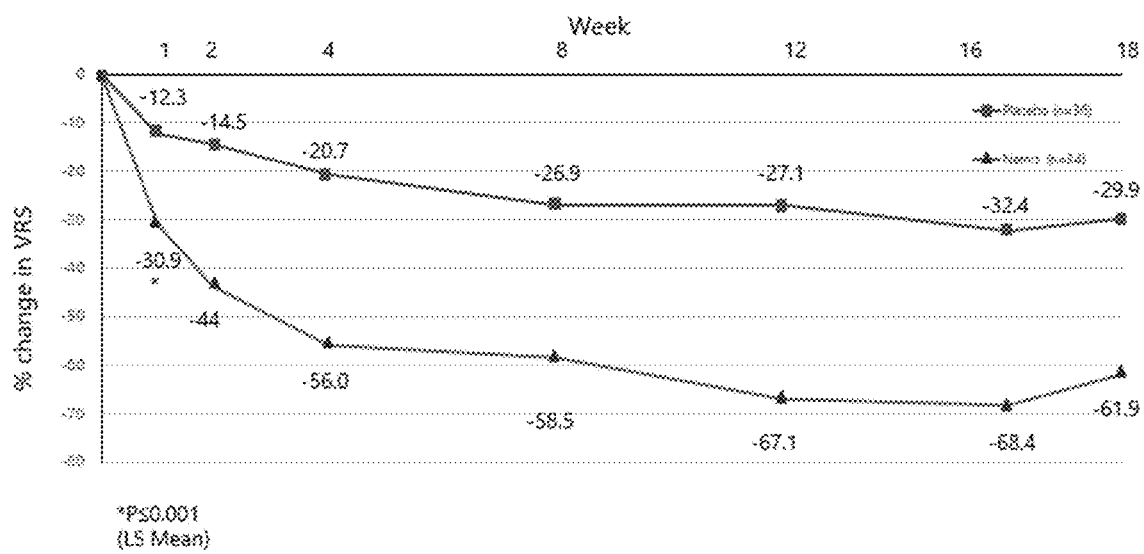
FIG. 9 illustrates percentage change in verbal rating scale (VRS) over 18 week treatment. The verbal rating scale (VRS) is a monodimensional scale that allows patients to describe their itch intensity by means of gradually rising adjectives.

Verbal rating scale (VRS) is a monodimensional scale that allows patients to describe their itch intensity by means of gradually rising adjectives (1=no itch, and 4=very severe itch). In other words, the nemolizumab treatment group shows consistently higher percentage change in negative value, which translates into more reduced itchiness throughout the 18 weeks study compared to the placebo group (FIG. 9). The results are statistically significant (p<0.001).

Figure 10:
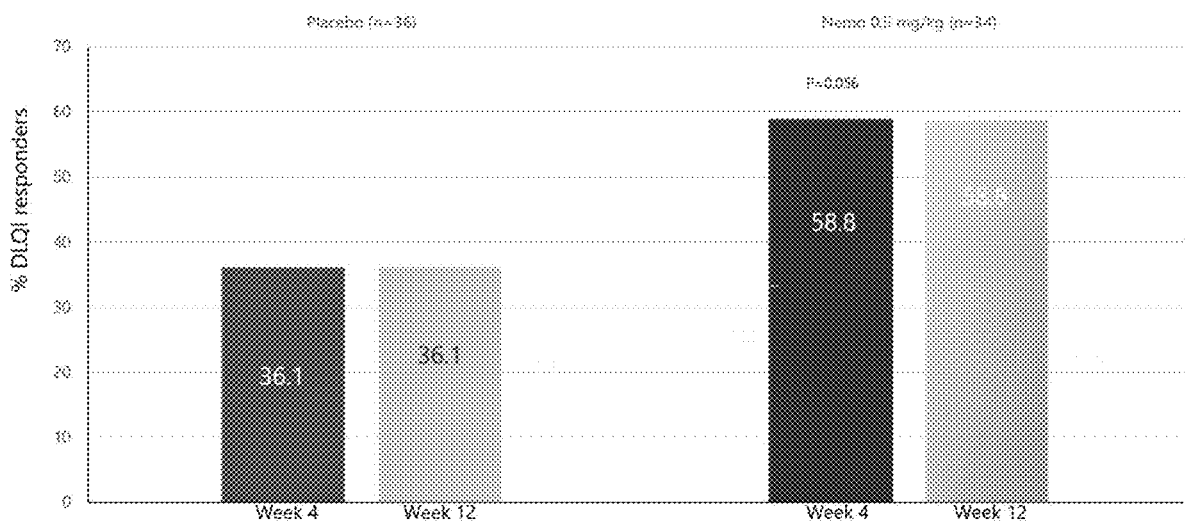
FIG. 10 illustrates dermatology life quality index (DLQI) Responders (>4) at Week 4 and Week 12. Dermatology Life Quality Index (DLQI) scores range from 0 to 30, with higher scores indicating a lower quality of life.
Figure 11:
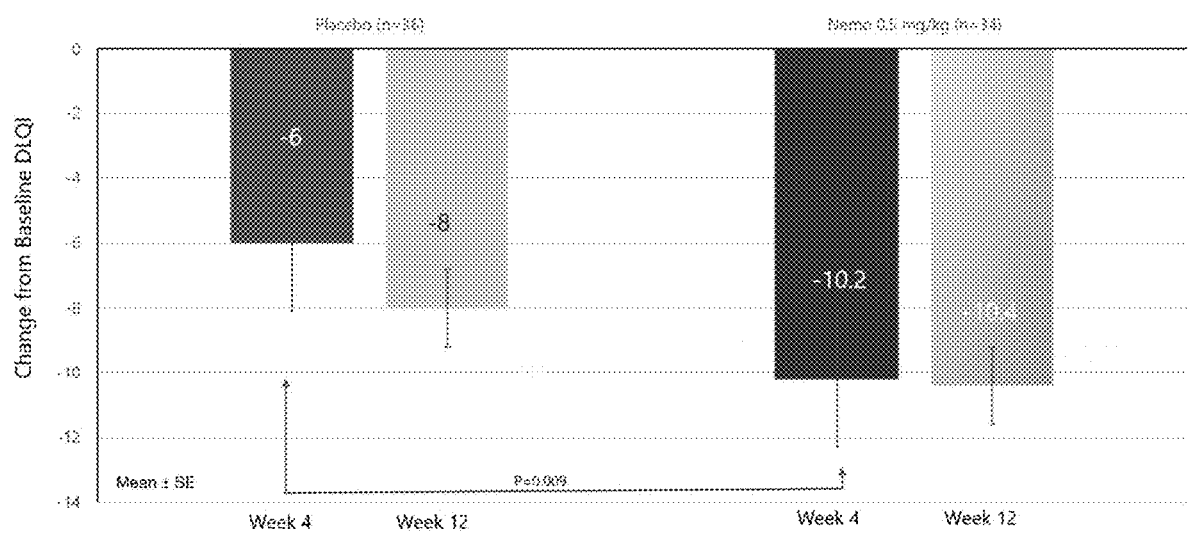
FIG. 11 illustrates change from baseline in DLQI at Week 4 and Week 12.
Figure 12A:
FIGS. 12A-12D compare full body images of patients before nemolizumab treatment (A and C) and after treatment for 16 weeks (B and D).
Figure 12B:
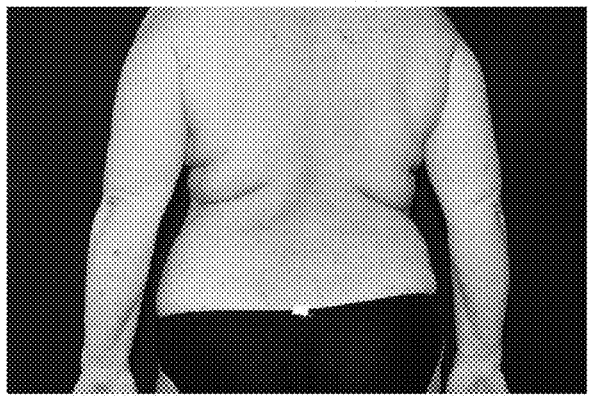
Figure 12C:
Figure 12D:
Figure 13A:
FIGS. 13A-13D compare full body images of patients before nemolizumab treatment (A and C) and after treatment for 16 weeks (B and D).
Figure 13B:
Figure 13C:
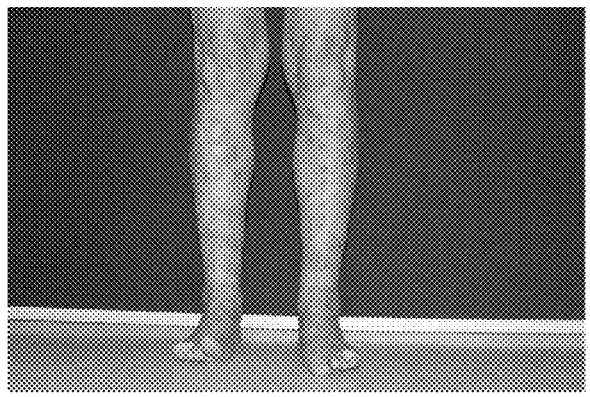
Figure 13D:
Figure 14A:
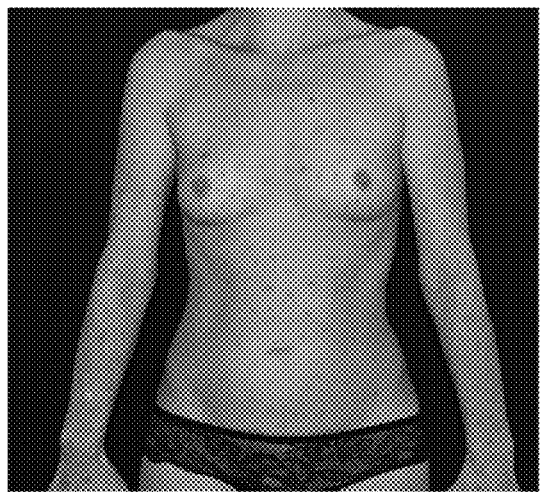
FIGS. 14A-14D compare full body images of patients before nemolizumab treatment (A and C) and after treatment for 16 weeks (B and D).
Figure 14B:
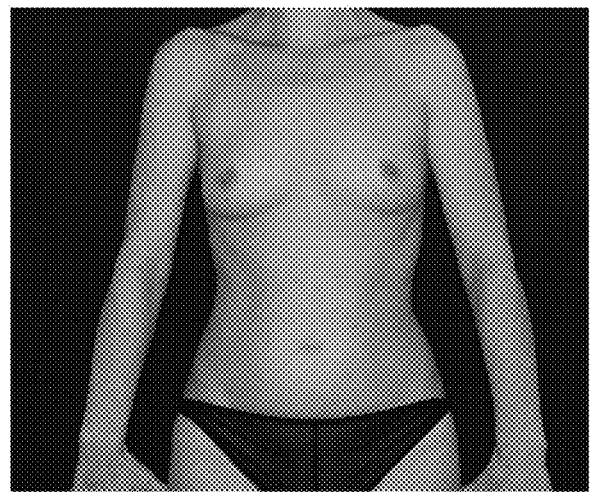
Figure 14C:
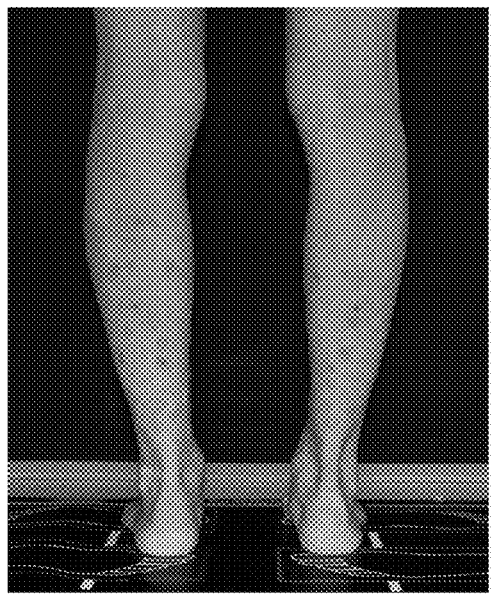
Figure 14D:
Figure 15:
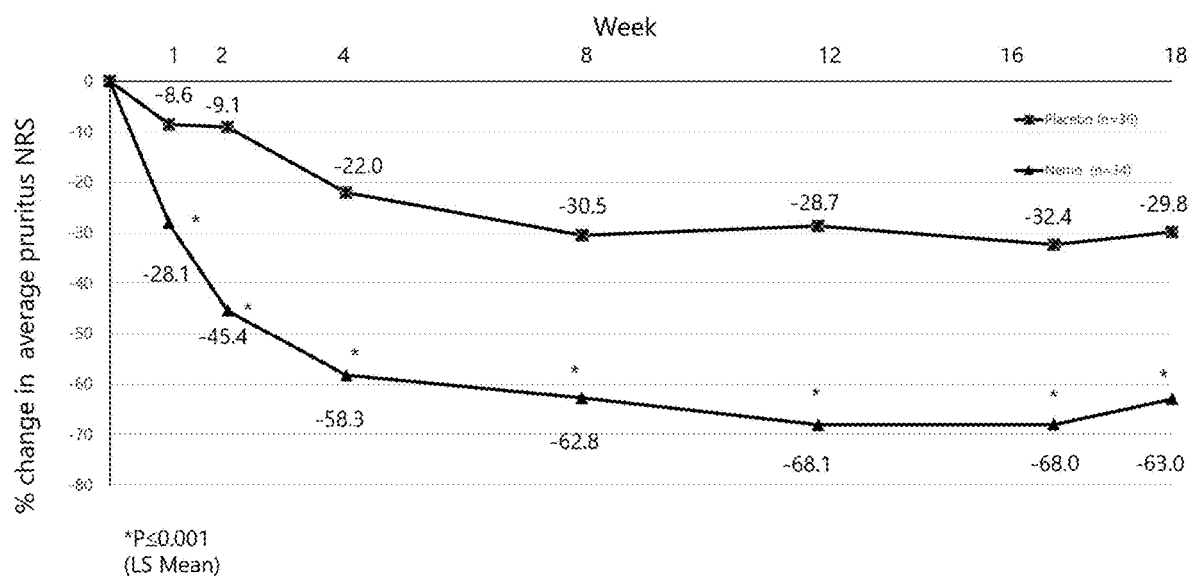
FIG. 15 illustrates percentage change in average pruritus Numerical Rating Scale (NRS) over 18 week treatment.
Figure 16:
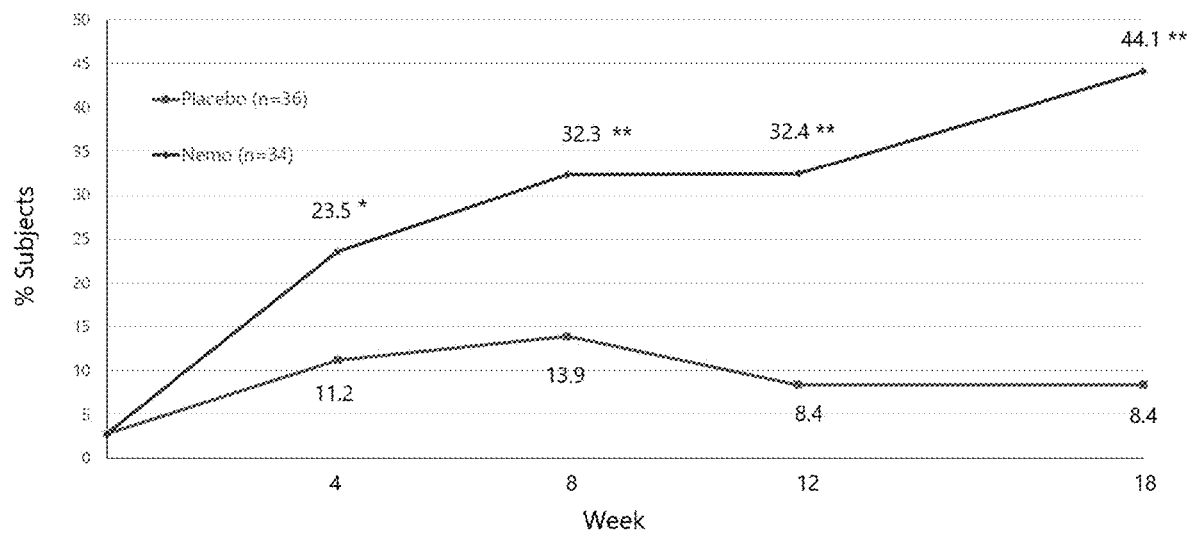
FIG. 16 illustrates proportion of subjects with Prurigo Activity Score (PAS) 75% healed over 18 week treatment.
Figure 17:
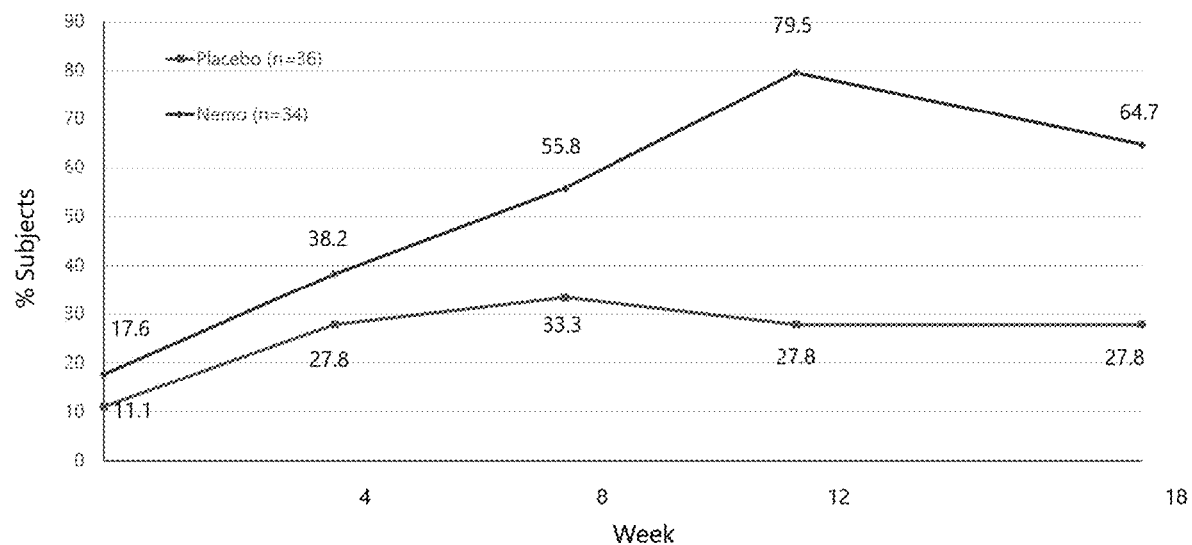
FIG. 17 illustrates proportion of subjects with Prurigo Activity Score (PAS) 50% healed over 18 week treatment.
Figure 18:
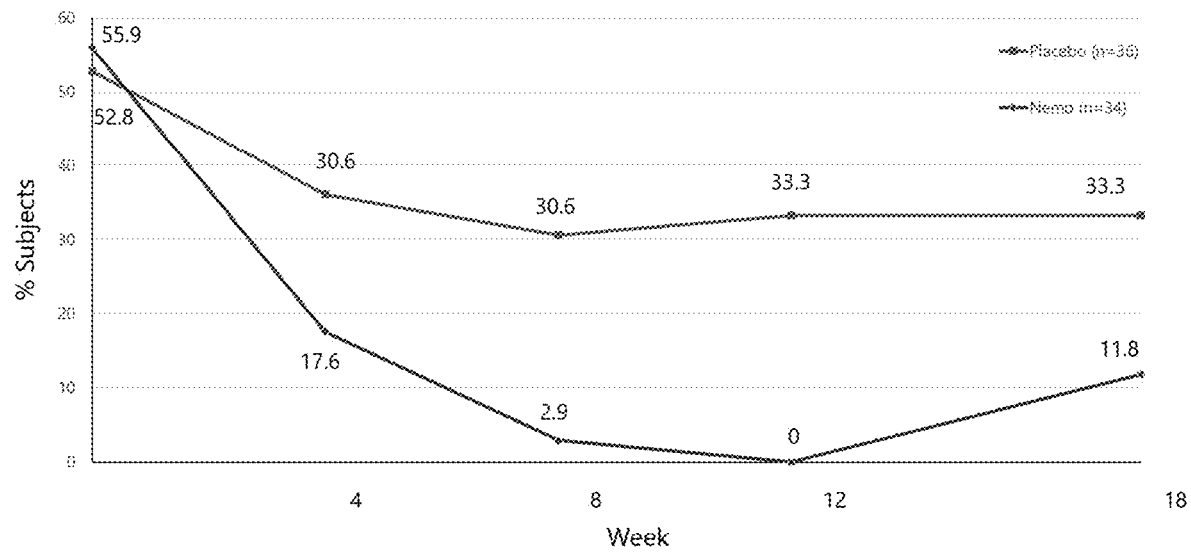
FIG. 18 illustrates proportion of subjects with Prurigo Activity Score (PAS) 0-24% healed over 18 week treatment.
Figure 19:
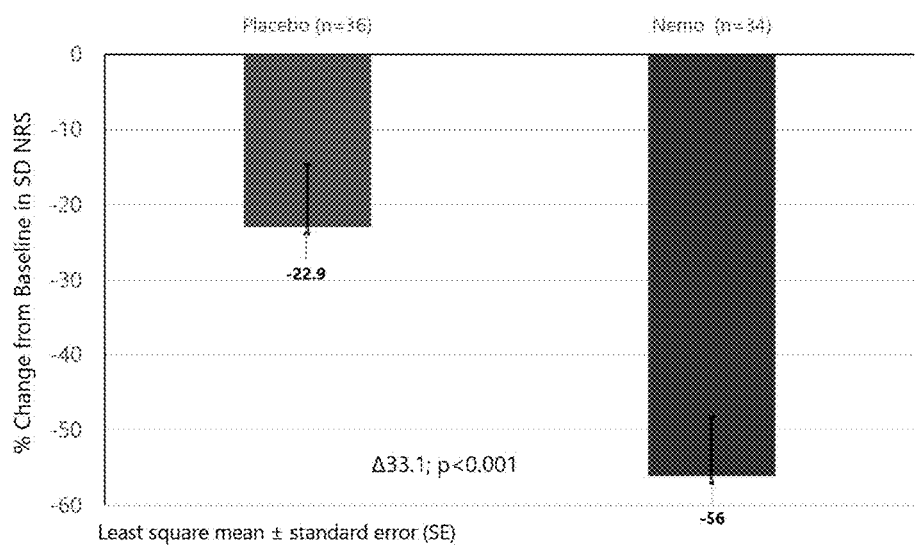
FIG. 19 illustrates percentage change from baseline in sleep disturbance NRS at week 4.
Figure 20:
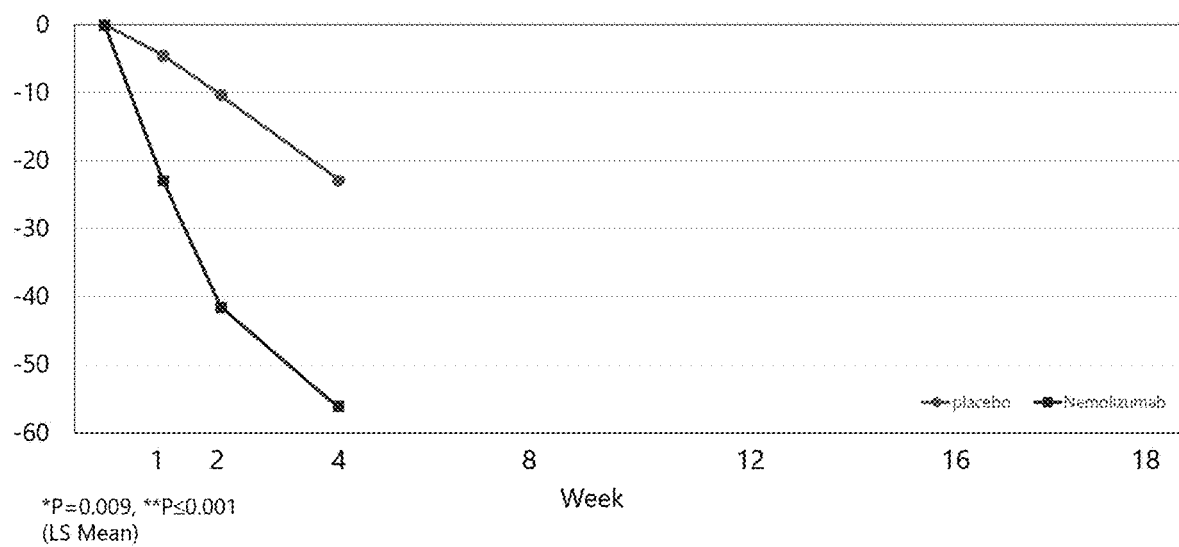
FIG. 20 illustrates percentage change in sleep disturbance NRS at week 4.

Dermatology Life Quality Index (DLQI) scores range from 0 to 30, with higher scores indicating a lower quality of life. As shown in FIG. 10, the nemolizumab treatment group has a higher percentage of responders rating DLQI ≥4 compared to the placebo group both at week 4 and week 12. As shown in FIG. 11, change from baseline in DLQI is statistically significant (p<0.01) in favor of nemolizumab at week 4 but not at week 12.

Full body images were taken of representative patients. As shown by FIGS. 12A-12D, 13A-13D, and 14A-14D, nemolizumab treatment significantly reduced the number of nodules on patient's body after 16 weeks.

Preliminary Safety Results

As shown in Tables 6 and 7, the nemolizumab treatment group and the placebo group shows comparable numbers of treatment emergent adverse events (TEAEs) of all causes, and comparable incidence of TEAEs by system organ class (SOC) of all causes. Overall nemolizumab was well tolerated.

TABLE 6

Safety-overall summary of treatment emergent adverse events (TEAEs) of all causes

|  | Placebo (N = 36) | Nemolizumab 0.5 mg/kg (N = 34) | Total (N = 70) |
|---|---|---|---|
| Number of TEAEs | 69 | 77 | 146 |
| Subjects with at least one TEAE | 24 (66.7%) | 23 (67.6%) | 47 (67.1%) |
| Serious TEAE | 3 (8.3%) | 4 (11.8%) | 7 (10.0%) |
| Severe TEAE | 1 (2.8%) | 5 (14.7%) | 6 (8.6%) |
| Fatal TEAE | 0 | 0 | 0 |
| TEAE leading to temporary drug discontinuation | 1 (2.8%) | 0 | 1 (1.4%) |
| TEAE leading to permanent drug discontinuation | 1 (2.8%) | 2 (5.9%) | 3 (4.3%) |
| TEAE leading to withdrawal | 2 (5.6%) | 2 (5.9%) | 4 (5.7%) |

TABLE 7

Incidence of TEAEs by System Organ Class (SOC) (>5%), all causes

|  | Placebo (N = 36) | Nemolizumab 0.5 mg/kg (N = 34) | Total (N = 70) |
|---|---|---|---|
| Infections and infestation | 12 (33.3%) | 10 (29.4%) | 22 (31.4%) |
| Skin and subcutaneous tissue disorders | 12 (33.3%) | 10 (29.4%) | 22 (31.4%) |
| Gastrointestinal disorders | 5 (13.9%) | 7 (20.6%) | 12 (17.1%) |
| Musculoskeletal and connective tissue disorders | 5 (13.9%) | 6 (17.6%) | 11 (15.7%) |
| General disorders and administration site conditions | 4 (11.1%) | 5 (14.7%) | 9 (12.9%) |
| Injury, poisoning and procedural complication | 2 (5.6%) | 4 (11.8%) | 6 (8.6%) |
| Renal and urinary disorders | 2 (5.6%) | 2 (5.9%) | 4 (5.7%) |
| Nervous system disorders | 1 (2.8%) | 2 (5.9%) | 3 (4.3%) |
| Respiratory, thoracic and mediastatial disorders | 3 (8.3%) | 0 | 3 (4.3%) |
| Blood and lymphatic system disorders | 2 (5.6%) | 0 | 2 (2.9%) |
| Metabolism and nutrition disorders | 0 | 2 (5.9%) | 2 (2.9%) |
| Psychiatric disorders | 2 (5.6%) | 0 | 2 (2.9%) |
| Vascular disorders | 2 (5.6%) | 0 | 2 (2.9%) |

What is claimed is:

1. A method of treating skin lesions and pruritus in a subject having chronic prurigo (CP), the method comprising administering an effective amount of nemolizumab or an equivalent thereof to the subject, wherein the subject does not have atopic dermatitis.

2. The method claim 1, wherein the subject has at least about 20 nodules on his/her body with a bilateral distribution.

3. The method of claim 1, wherein the subject has prurigo lesions on upper limbs.

4. The method of claim 1, wherein the pruritus has been assigned a score of at least 4 on the Numerical Rating Scale (NRS).

5. The method of claim 1, wherein the pruritus has been assigned a score of at least 7 on the Numerical Rating Scale (NRS).

6. The method of claim 1, wherein the effective amount of nemolizumab or the equivalent thereof is about 0.01 mg/kg to about 0.1 mg/kg, about 0.1 mg/kg to about 0.5 mg/kg, about 0.5 mg/kg to about 1.5 mg/kg, about 1.5 mg/kg to about 2.5 mg/kg, or about 2.5 mg/kg to about 10 mg/kg.

7. The method of claim 1, wherein the effective amount of nemolizumab or the equivalent thereof is about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg.

8. The method of claim 1, wherein the nemolizumab or equivalent thereof is administered according to a flat dosing regimen.

9. The method of claim 1, wherein the nemolizumab or equivalent thereof is administered according to a loading dose regimen.

10. The method of claim 1, wherein the nemolizumab or the equivalent thereof is administered by a topical or parenteral route.

11. The method of claim 1, wherein the nemolizumab or the equivalent thereof is administered subcutaneously.

12. The method of claim 1, wherein the nemolizumab or the equivalent thereof is administered once per week, once every two weeks, once every three weeks, once every four weeks, once every five weeks, once every six weeks, once every seven weeks, or once every eight weeks.

13. The method of claim 1, wherein the chronic prurigo is prurigo nodularis (PN).

14. The method of claim 13, wherein the subject has been diagnosed of PN for at least about 6 months.

15. The method claim 13, wherein the subject has at least about 20 nodules on his/her body with a bilateral distribution.

16. The method of claim 13, wherein the subject has prurigo lesions on upper limbs.

17. The method of claim 13, wherein the pruritus has been assigned a score of at least 4 on the Numerical Rating Scale (NRS).

18. The method of claim 13, wherein the pruritus has been assigned a score of at least 7 on the Numerical Rating Scale (NRS).

19. The method of claim 13, wherein the effective amount of nemolizumab or the equivalent thereof is about 0.01 mg/kg to about 0.1 mg/kg, about 0.1 mg/kg to about 0.5 mg/kg, about 0.5 mg/kg to about 1.5 mg/kg, about 1.5 mg/kg to about 2.5 mg/kg, or about 2.5 mg/kg to about 10 mg/kg.

20. The method of claim 13, wherein the effective amount of nemolizumab or the equivalent thereof is about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg.

21. The method of claim 13, wherein the nemolizumab or equivalent thereof is administered according to a flat dosing regimen.

22. The method of claim 13, wherein the nemolizumab or equivalent thereof is administered according to a loading dose regimen.

23. The method of claim 13, wherein the nemolizumab or the equivalent thereof is administered by a topical or parenteral route.

24. The method of claim 13, wherein the nemolizumab or the equivalent thereof is administered subcutaneously.

25. The method of claim 13, wherein the nemolizumab or the equivalent thereof is administered once per week, once every two weeks, once every three weeks, once every four weeks, once every five weeks, once every six weeks, once every seven weeks, or once every eight weeks.

* * * * *